United States Patent
Kato et al.

(10) Patent No.: US 11,225,624 B2
(45) Date of Patent: Jan. 18, 2022

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Tsuyoshi Kato, Ichihara (JP); Daisuke Yagyu, Ichihara (JP); Naoya Fukumoto, Ichihara (JP); Yuta Yamaguchi, Kawasaki (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/643,989

(22) PCT Filed: Aug. 7, 2018

(86) PCT No.: PCT/JP2018/029582
§ 371 (c)(1),
(2) Date: Mar. 3, 2020

(87) PCT Pub. No.: WO2019/049585
PCT Pub. Date: Mar. 14, 2019

(65) Prior Publication Data
US 2021/0062101 A1 Mar. 4, 2021

(30) Foreign Application Priority Data
Sep. 7, 2017 (JP) .............................. JP2017-172415

(51) Int. Cl.
*C10M 105/54* (2006.01)
*G11B 5/725* (2006.01)
(Continued)

(52) U.S. Cl.
CPC ........ *C10M 105/54* (2013.01); *C10M 107/38* (2013.01); *G11B 5/7257* (2020.08);
(Continued)

(58) Field of Classification Search
CPC .............. C10M 105/54; C10M 107/38; C10M 2213/043; C10N 2040/18; C10N 2020/04;
(Continued)

(56) References Cited

U.S. PATENT DOCUMENTS 5,049,410 A   9/1991  Johary et al.
8,668,995 B2 * 3/2014  Shimizu ................. C07C 43/23
                                                    428/835.8
(Continued)

FOREIGN PATENT DOCUMENTS

JP    3-153645 A   7/1991
JP    4632144 B2   2/2011
(Continued)

OTHER PUBLICATIONS

International Search Report for PCT/JP2018/029582 dated Nov. 6, 2018 [PCT/ISA/210].

*Primary Examiner* — James C Goloboy
(74) *Attorney, Agent, or Firm* — Sughrue Mion, PLLC

(57) ABSTRACT

A fluorine-containing ether compound represented by Formula (1) is provided, $$R^1-R^2-CH_2-R^3-CH_2-R^4 \quad (1)$$

(In Formula (1), $R^1$ is an alkyl group that may have a substituent, $R^2$ is a divalent linking group bonded to $R^1$ via an ethereal oxygen, $R^3$ is a perfluoropolyether chain, and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups.).

16 Claims, 1 Drawing Sheet

(51) Int. Cl.
*C10M 107/38* (2006.01)
*G11B 5/82* (2006.01)
*C10N 40/18* (2006.01)
*C10N 50/00* (2006.01)
*C10N 20/04* (2006.01)
*C10N 50/02* (2006.01)
*C10N 30/06* (2006.01)

(52) U.S. Cl.
CPC .......... *G11B 5/82* (2013.01); *C10M 2213/043* (2013.01); *C10N 2020/04* (2013.01); *C10N 2030/06* (2013.01); *C10N 2040/18* (2013.01); *C10N 2050/02* (2013.01); *C10N 2050/025* (2020.05)

(58) Field of Classification Search
CPC ............ C10N 2030/06; C10N 2050/02; C10N 2050/025; G11B 5/82; G11B 5/7257
See application file for complete search history.

(56) References Cited

U.S. PATENT DOCUMENTS

| | | |
|---|---|---|
| 2012/0315504 A1 | 12/2012 | Shimizu et al. |
| 2017/0152456 A1 | 6/2017 | Sagata et al. |
| 2017/0260472 A1* | 9/2017 | Sagata ................... C07C 43/03 |
| 2020/0263104 A1* | 8/2020 | Yamaguchi ............ G11B 5/725 |

FOREIGN PATENT DOCUMENTS

| | | | |
|---|---|---|---|
| JP | 2013-018961 A | 1/2013 | |
| JP | 5465454 B2 | 4/2014 | |
| JP | 5909837 B2 | 4/2016 | |
| WO | 2015/022871 A1 | 2/2015 | |
| WO | 2015/199037 A1 | 12/2015 | |
| WO | 2016/084781 A1 | 6/2016 | |
| WO | 2017/145995 A1 | 8/2017 | |
| WO | WO-2017145995 A1 * | 8/2017 | ............ G11B 5/725 |

* cited by examiner

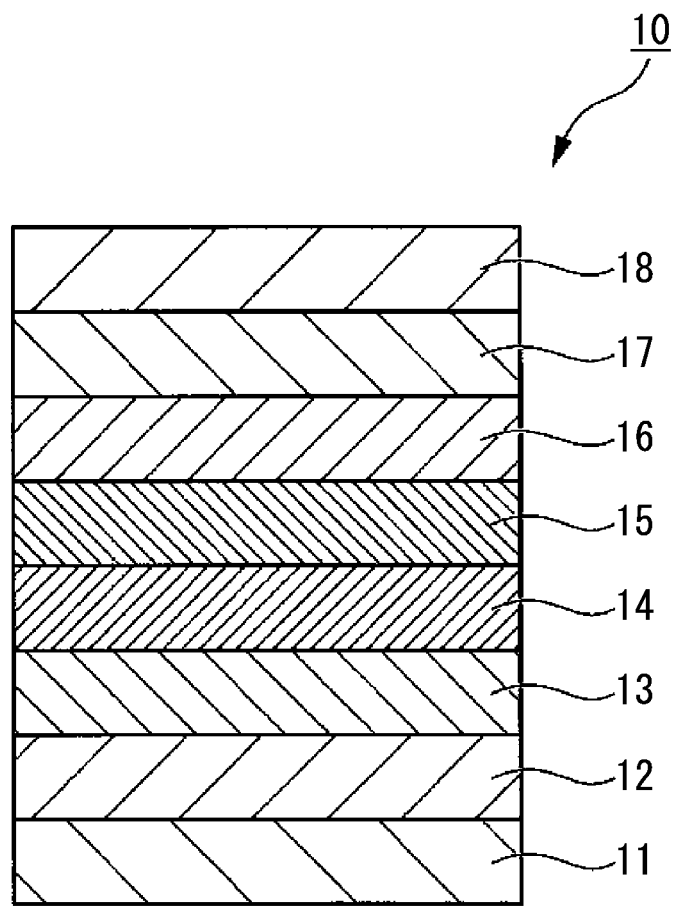

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2018/029582 filed Aug. 7, 2018, claiming priority based on Japanese Patent Application No. 2017-172415 filed Sep. 7, 2017.

TECHNICAL FIELD

The present invention relates to a fluorine-containing ether compound suitable for a lubricant application of a magnetic recording medium, and a lubricant for a magnetic recording medium and a magnetic recording medium which includes the same.

BACKGROUND ART

In order to improve recording density of a magnetic recording and reproducing apparatus, development of a magnetic recording medium suitable for high recording density is in progress.

In the related art, there is a magnetic recording medium in which a recording layer is formed on a substrate and a protective layer made of carbon is formed on the recording layer. The protective layer protects information recorded in the recording layer and enhances slidability of a magnetic head. However, durability of the magnetic recording medium cannot be sufficiently obtained simply by providing the protective layer on the recording layer. Therefore, in general, a lubricating layer is formed by applying a lubricant to a surface of the protective layer.

As a lubricant used when forming the lubricating layer for the magnetic recording medium, for example, a lubricant is proposed including a compound having a polar group such as a hydroxyl group at an end of a fluorine polymer having a repeating structure containing $CF_2$ (for example, see Patent Documents 1 to 4).

For example, Patent Document 1 discloses a compound including a substituent, which has a plurality of hydroxyl groups, at both end parts, in which a shortest distance between the hydroxyl groups is 3 atoms or more. In addition, Patent Document 2 discloses a fluoropolyether compound having an aromatic group at one end and a hydroxyl group at the other end. In addition, Patent Document 3 discloses a compound including a perfluoropolyether main chain, and an aromatic group and a hydroxyl group at an end of a molecule, in which the aromatic group and the hydroxyl group are bonded to different carbon atoms. In addition, Patent Document 4 discloses a fluoropolyether compound having an alkyl group at one end and a hydroxyl group at the other end.

CITATION LIST

Patent Documents

Patent Document 1: Japanese Patent No. 4632144
Patent Document 2: Japanese Patent No. 5909837
Patent Document 3: Japanese Patent No. 5465454
Patent Document 4: PCT international Publication No. WO2015/199037

DISCLOSURE OF INVENTION

Technical Problem

In a magnetic recording and reproducing apparatus, it is required to further reduce the flying height of a magnetic head. Therefore, it is required to make a thickness of a lubricating layer in a magnetic recording medium thinner.

However, in general, when the thickness of the lubricating layer is reduced, coatability of the lubricating layer tends to decrease and chemical resistance and wear resistance of the magnetic recording medium tend to decrease.

The present invention was made in view of the circumstances, and an object thereof is to provide a fluorine-containing ether compound which can be suitably used as a material of a lubricant for a magnetic recording medium, which can form a lubricating layer having excellent chemical resistance and wear resistance, even when the thickness is reduced.

In addition, another object of the present invention is to provide a lubricant for a magnetic recording medium including the fluorine-containing ether compound of the present invention.

In addition, still another object of the present invention is to provide a magnetic recording medium which includes a lubricating layer including the fluorine-containing ether compound of the present invention and has excellent reliability and durability.

Solution to Problem

The present inventors have intensively studied to achieve the above objects.

As a result, it was found that a fluorine-containing ether compound in which an alkyl group that may have a substituent is placed on one end of a perfluoropolyether chain via a divalent linking group bonded to the alkyl group via an ethereal oxygen, and an end group, which includes two or three polar groups, in which each of the polar groups is bonded to a different carbon atom, and the carbon atoms bonded to the polar groups are bonded to each other via a linking group containing a carbon atom not bonded to the polar groups, is placed on the other end of the perfluoropolyether chain may be used, and the present invention was conceived.

That is, the present invention relates to the following aspects.

[1] A fluorine-containing ether compound represented by Formula (1).

(In Formula (1), $R^1$ is an alkyl group that may have a substituent, $R^2$ is a divalent linking group bonded to $R^1$ via an ethereal oxygen, $R^3$ is a perfluoropolyether chain, and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups)

[2] The fluorine-containing ether compound according to [1], in which the polar groups of $R^4$ in Formula (1) are hydroxyl groups.

[3] The fluorine-containing ether compound according to [1] or [2], in which $R^4$ in Formula (1) is an end group represented by any one of Formulas (2-1) to (2-4).

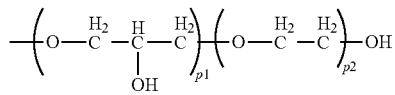
(2-1)

(In Formula (2-1), p1 represents 1 to 2 and p2 represents 1 to 5)

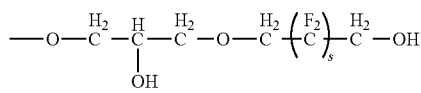
(2-2)

(In Formula (2-2), s represents 2 to 5)

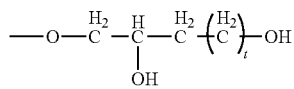
(2-3)

(In Formula (2-3), t represents 1 to 5)

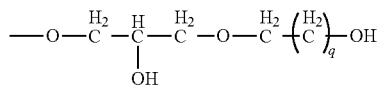
(2-4)

(In Formula (2-4), q represents 2 to 5)

[4] The fluorine-containing ether compound according to any one of [1] to [3], in which $R^3$ in Formula (1) is represented by Formula (3).

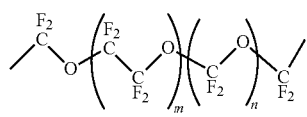
(3)

(In Formula (3), m and n represent average polymerization degrees, m represents 1 to 30, and n represents 0 to 30)

[5] The fluorine-containing ether compound according to any one of [1] to [3], in which $R^3$ in Formula (1) is represented by Formula (4) or (5).

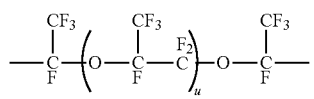
(4)

(In Formula (4), u represents an average polymerization degree and represents 1 to 30)

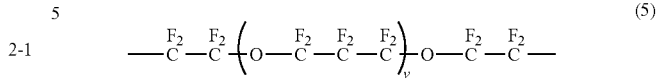
(5)

(In Formula (5), v represents an average polymerization degree and represents 1 to 30)

[6] The fluorine-containing ether compound according to any one of [1] to [5], in which $R^1$ in Formula (1) is an alkyl group in which a part or all of hydrogen atoms are substituted with halogen and/or an alkoxy group.

[7] The fluorine-containing ether compound according to any one of [1] to [6], in which $R^2$ in Formula (1) is represented by —O— or Formula (6).

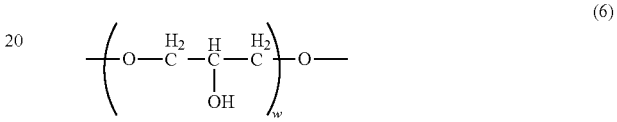
(6)

(In Formula (6), w represents 1 to 4)

[8] The fluorine-containing ether compound according to any one of [1] to [7], in which $R^4$ in Formula (1) includes three polar groups. [9] The fluorine-containing ether compound according to any one of [1] to [8], in which a number-average molecular weight thereof is in a range of 500 to 10000.

[10] A lubricant for a magnetic recording medium, including the fluorine-containing ether compound according to any one of [1] to [9].

[11] A magnetic recording medium, including: a substrate; and at least a magnetic layer, a protective layer, and a lubricating layer in this order on the substrate, in which the lubricating layer includes the fluorine-containing ether compound according to any one of [1] to [9].

[12] The magnetic recording medium according to [11], in which an average film thickness of the lubricating layer is 0.5 nm to 3 nm.

Advantageous Effects of Invention

The fluorine-containing ether compound of the present invention is suitable as a material of a lubricant for a magnetic recording medium.

Since the lubricant for a magnetic recording medium of the present invention includes the fluorine-containing ether compound of the present invention, it is possible to form a lubricating layer in which excellent chemical resistance and wear resistance are obtained even when the thickness is reduced.

The magnetic recording medium of the present invention is provided with a lubricating layer having excellent chemical resistance and wear resistance, and thus has excellent reliability and durability.

BRIEF DESCRIPTION OF DRAWINGS

FIG. 1 is a schematic sectional view showing an embodiment of a magnetic recording medium according to the present invention.

BEST MODE FOR CARRYING OUT THE INVENTION

Hereinafter, a fluorine-containing ether compound, a lubricant for a magnetic recording medium (hereinafter sometimes abbreviated as a "lubricant"), and a magnetic recording medium of the present invention will be described in detail. The present invention is not limited to only the embodiments shown below. For example, the present invention is not limited to only the following examples, and addition, omission, substitution, or a change in the number, the amount, a ratio, a material, a configuration, and the like can be made within the scope not departing from the gist of the present invention.

[Fluorine-Containing Ether Compound]

The fluorine-containing ether compound of the present embodiment is represented by Formula (1).

(In Formula (1), $R^1$ is an alkyl group that may have a substituent, $R^2$ is a divalent linking group bonded to $R^1$ via an ethereal oxygen, $R^3$ is a perfluoropolyether chain, and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups.)

Here, in a case where a lubricating layer is formed on a protective layer of the magnetic recording medium by using a lubricant including the fluorine-containing ether compound of the present embodiment, the reason why excellent chemical resistance and wear resistance are obtained even when a thickness is reduced will be described.

In the fluorine-containing ether compound of the present embodiment, as shown in Formula (1), an alkyl group represented by $R^1$ that may have a substituent is placed on one end of a perfluoropolyether chain (hereinafter sometimes abbreviated as a "PFPE chain") represented by $R^3$ via a divalent linking group, bonded to $R^1$ via an ethereal oxygen, represented by $R^2$. In the lubricating layer including the fluorine-containing ether compound of the present embodiment, the PFPE chain covers the surface of the protective layer and reduces frictional force between the magnetic head and the protective layer. In addition, the alkyl group represented by $R^1$ that may have a substituent improves chemical resistance and wear resistance in the lubricating layer including the fluorine-containing ether compound of the present embodiment, by an intermolecular interaction of the alkyl group that may have a substituent and/or an interaction between the alkyl group that may have a substituent and the protective layer. Therefore, in the lubricating layer including the fluorine-containing ether compound of the present embodiment, for example, excellent chemical resistance and wear resistance are obtained, compared to a lubricating layer including a fluorine-containing ether compound in which a hydroxyl group is placed instead of the alkyl group represented by $R^1$ that may have a substituent.

In addition, an end group represented by $R^4$ is placed at an end (the other end) opposed to $R^2$ of the PFPE chain represented by $R^3$ in Formula (1). The end group represented by $R^4$ includes two or three polar groups. In the lubricating layer including the fluorine-containing ether compound of the present embodiment, the two or three polar groups included in the end group represented by $R^4$ bring the fluorine-containing ether compound and the protective layer into close contact with each other to improve chemical resistance and wear resistance and suppresses pickup.

In addition, in the lubricating layer, two or three polar groups included in the end group represented by $R^4$ are bonded to different carbon atoms respectively, and the carbon atoms bonded to the polar groups are bonded to each other via a linking group containing a carbon atom not bonded to the polar groups. The fluorine-containing ether compound having an end group represented by $R^4$ is less likely to aggregate, for example, compared to a fluorine ether compound in which two polar groups included in an end group are bonded to different carbon atoms respectively, and the carbon atoms bonded to the polar groups are bonded to each other. Accordingly, in the lubricating layer including the fluorine-containing ether compound of the present embodiment, it is possible to prevent the fluorine-containing ether compound not adhering (adsorbing) to the protective layer from aggregating and adhering to a magnetic head as foreign substance (smear), and pickup is suppressed. In addition, since the fluorine-containing ether compounds are less likely to aggregate with each other, the fluorine-containing ether compound in the lubricating layer is likely to be placed in a state of extending in a plane direction on the protective layer. Accordingly, it is presumed that, with the lubricant including the fluorine-containing ether compound, a lubricating layer having excellent chemical resistance, with which a surface of the protective layer can be covered with high coverage can be formed even when a thickness is reduced.

In the fluorine-containing ether compound represented by Formula (1) of the present embodiment, $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups. The end group represented by $R^4$ contributes to adhesion between the protective layer to which a lubricant including the fluorine-containing ether compound of the present embodiment is applied, and the lubricating layer formed by applying the lubricant. $R^4$ in Formula (1) can be appropriately selected according to a performance or the like required for the lubricant including the fluorine-containing ether compound.

In addition, the fluorine-containing ether compound represented by Formula (1) of the present embodiment is an asymmetric compound in which different groups ($R^1$ and $R^4$) are bonded to both ends of the PFPE chain ($R^3$) respectively. In the compound in which different groups are bonded to both ends respectively, further excellent chemical resistance and wear resistance are obtained by a synergistic effect of the groups ($R^1$ and $R^4$) having different functions, respectively bonded to the molecular ends, compared to a compound in which the same end groups are bonded to both ends respectively.

Examples of the polar group in $R^4$ include a hydroxyl group, an amino group, a carboxyl group, and a mercapto group. The ether bond (—O—) is not included in the polar group in $R^4$.

Since a lubricating layer including a fluorine-containing ether compound having favorable adhesion to the protective layer can be obtained, the polar group in the end group of $R^4$ including two or three polar groups is preferably the hydroxyl group.

$R^4$ in Formula (1) is preferably an end group represented by any one of Formulas (2-1) to (2-4). This $R^4$ contributes to high adhesion and coverage between the protective layer to which the lubricant including a fluorine-containing ether compound of the present embodiment is applied, and the lubricating layer formed by applying the lubricant.

$$-\left(O-\overset{H_2}{C}-\overset{H}{\underset{OH}{C}}-\overset{H_2}{C}\right)_{p1}\left(O-\overset{H_2}{C^2}-\overset{H_2}{C^2}\right)_{p2}-OH \quad (2\text{-}1)$$

(In Formula (2-1), p1 represents 1 to 2 and p2 represents 1 to 5.)

In Formula (2-1), p1 is 1 to 2.

In Formula (2-1), in a case where p2 is 1 to 5, the distance between the hydroxyl groups in the end group represented by Formula (2-1) is appropriate, and a lubricating layer having excellent adhesion to the protective layer and high coverage can be formed. p2 is preferably 1 to 2, and most preferably 1.

$$-O-\overset{H_2}{C}-\overset{H}{\underset{OH}{C}}-\overset{H_2}{C}-O-\overset{H_2}{C}-\left(\overset{F_2}{C}\right)_s-\overset{H_2}{C}-OH \quad (2\text{-}2)$$

(In Formula (2-2), s represents 2 to 5.)

In Formula (2-2), in a case where s is 2 to 5, the distance between the hydroxyl group on the $R^3$ side and the hydroxyl group at the end is appropriate, and a lubricating layer having excellent adhesion to the protective layer and high coverage can be formed. s is preferably 2 to 3, and most preferably 2.

$$-O-\overset{H_2}{C}-\overset{H}{\underset{OH}{C}}-\overset{H_2}{C}-\left(\overset{H_2}{C}\right)_t-OH \quad (2\text{-}3)$$

(In Formula (2-3), t represents 1 to 5.)

In Formula (2-3), in a case where t is 1 to 5, the distance between the hydroxyl group on the $R^3$ side and the hydroxyl group at the end is appropriate, and a lubricating layer having excellent adhesion to the protective layer and high coverage can be formed.

t is preferably 1 to 2, and most preferably 1.

$$-O-\overset{H_2}{C}-\overset{H}{\underset{OH}{C}}-\overset{H_2}{C}-O-\overset{H_2}{C}-\left(\overset{H_2}{C}\right)_q-OH \quad (2\text{-}4)$$

(In Formula (2-4), q represents 2 to 5.)

In Formula (2-4), in a case where q is 2 to 5, the distance between the hydroxyl group on the $R^3$ side and the hydroxyl group at the end is appropriate, and a lubricating layer having excellent adhesion to the protective layer and high coverage can be formed. q is preferably 2 to 3.

In Formula (1), $R^3$ is a perfluoropolyether chain (PFPE chain). In a case where the lubricant including the fluorine-containing ether compound is applied onto the protective layer to form the lubricating layer, the PFPE chain covers the surface of the protective layer and imparts lubricity to the lubricating layer to reduce frictional force between a magnetic head and the protective layer.

$R^3$ is not particularly limited, and can be appropriately selected according to a performance or the like required for the lubricant including the fluorine-containing ether compound.

$R^3$ in Formula (1) is preferably a PFPE chain represented by Formula (3) because a fluorine-containing ether compound is easily synthesized.

$$\overset{F_2}{C}-O-\left(\overset{F_2}{\underset{F_2}{C}}-O\right)_m\left(\overset{C}{\underset{F_2}{C}}-O\right)_n-\overset{C}{\underset{F_2}{C}}- \quad (3)$$

(In Formula (3), m and n represent average polymerization degrees, m represents 1 to 30, and n represents 0 to 30.)

In Formula (3), an arrangement order of $(CF_2-CF_2-O)$ and $(CF_2-O)$ which are repeating units is not particularly limited. In Formula (3), the number m of $(CF_2-CF_2-O)$ and the number n of $(CF_2-O)$, which indicate an average polymerization degree, may be the same as or different from each other. In Formula (3), any one of a random copolymer, a block copolymer, and an alternating copolymer including monomer units of $(CF_2-CF_2-O)$ and $(CF_2-O)$ may be included.

In a case where $R^3$ in Formula (1) is represented by Formula (3), m is 1 to 30, preferably 1 to 20, and more preferably 1 to 15. In Formula (1), in a case where $R^3$ is represented by Formula (3), n is 0 to 30, preferably 0 to 20, and more preferably 0 to 15. In addition, in a case where n is 0, m is preferably 1 to 17.

In Formula (1), $R^3$ may be represented by Formula (4) or (5).

$$-\overset{CF_3}{\underset{F}{C}}-\left(O-\overset{CF_3}{\underset{F}{C}}-\overset{F_2}{C}\right)_u-O-\overset{CF_3}{\underset{F}{C}}- \quad (4)$$

(In Formula (4), u represents an average polymerization degree and represents 1 to 30.)

In Formula (4), in a case where u is 1 to 30, the number-average molecular weight of the fluorine-containing ether compound of the present embodiment tends to be in a preferable range. u is preferably 3 to 20 and more preferably 4 to 10.

$$-\overset{F_2}{C}-\overset{F_2}{C}-\left(O-\overset{F_2}{C}-\overset{F_2}{C}-\overset{F_2}{C}\right)_v-O-\overset{F_2}{C}-\overset{F_2}{C}- \quad (5)$$

(In Formula (5), v represents an average polymerization degree and represents 1 to 30.)

In Formula (5), in a case where v is 1 to 30, the number-average molecular weight of the fluorine-containing ether compound of the present embodiment tends to be in a preferable range. v is preferably 3 to 20 and more preferably 4 to 10.

In a case where $R^3$ in Formula (1) is represented by any one of Formulas (3) to (5), the fluorine-containing ether compound is easily synthesized, which is preferable. In addition, in a case where $R^3$ in Formula (1) is represented by any one of Formulas (3) to (5), a ratio of the number of oxygen atoms (the number of ether bonds (—O—)) to the number of carbon atoms in the perfluoropolyether chain and an arrangement of oxygen atoms in the perfluoropolyether chain become appropriate. Therefore, a fluorine-containing ether compound having an appropriate rigidity is obtained. Accordingly, the fluorine-containing ether compound applied on the protective layer is less likely to aggregate on the protective layer, and the lubricating layer of which a thickness is thinner can be formed with sufficient coverage. In addition, in a case where $R^3$ in Formula (1) is represented by Formula (3), a raw material is easily available, which is more preferable.

$R^1$ in Formula (1) is an alkyl group that may have a substituent.

The alkyl group represented by $R^1$ preferably has 1 to 8 carbon atoms, and specific examples thereof include a methyl group, an ethyl group, a propyl group, a butyl group, a pentyl group, a hexyl group, a heptyl group, and an octyl group, which may be linear or branched.

In a case where the alkyl group represented by $R^1$ has a substituent, examples of the substituent include a halogeno group and/or an alkoxy group having 1 to 8 carbon atoms. In a case where $R^1$ is an alkyl group having a substituent, an alkyl group in which a part or all of hydrogen atoms are substituted with halogen is preferable, and an alkyl group in which a part or all of hydrogen atoms are substituted with fluorine is particularly preferable. When the alkyl group represented by $R^1$ that may have a substituent is an alkyl group having a fluoro group, a fluorine-containing ether compound capable of forming a lubricating layer having further excellent wear resistance is obtained.

Specific examples of the alkyl group having a fluoro group include a trifluoromethyl group, a perfluoroethyl group, a perfluoropropyl group, a perfluorobutyl group, a perfluoropentyl group, a perfluorohexyl group, an octafluoropentyl group, a tridecafluorooctyl group, a 1-methoxy-2,2,3,3,4,4,5,5-octafluoro-hexyl group, a 1-hydroxy-2,2,3,3,4,4,5,5-octafluoro-hexyl group, a 1-methoxy-1H,1H,11H,11H-dodecafluoro-3,6,9-trioxaundecane group, and a 1-hydroxy-1H,1H,11H,11H-dodecafluoro-3,6,9-trioxaundecane group.

Among these, the alkyl group having a fluoro group is preferably any one of the perfluorobutyl group, the perfluoropentyl group, the perfluorohexyl group, the octafluoropentyl group, the tridecafluorooctyl group, the 1-methoxy-2,2,3,3,4,4,5,5-octafluoro-hexyl group, the 1-hydroxy-2,2,3,3,4,4,5,5-octafluoro-hexyl group, the 1-methoxy-1H,1H,11H,11H-dodecafluoro-3,6,9-trioxaundecane group, and the 1-hydroxy-1H,1H,11H,11H-dodecafluoro-3,6,9-trioxaundecane group.

The alkyl group represented by $R^1$ having a substituent may be linear or branched.

$R^2$ in Formula (1) is a divalent linking group bonded to $R^1$ via an ethereal oxygen (—O—). The divalent linking group represented by $R^2$ is not particularly limited, as long as the linking group is bonded to $R^1$ by the ethereal oxygen, and can be appropriately selected according to a performance or the like required for the lubricant including the fluorine-containing ether compound.

The divalent linking group represented by $R^2$ preferably includes one or more polar groups, in order to improve adhesion between the protective layer to which a lubricant including the fluorine-containing ether compound is applied and the lubricating layer formed by applying the lubricant.

Examples of the polar group contained in the linking group include a hydroxyl group, a carboxyl group, an amino group, and an aminocarboxyl group, and the hydroxyl group is preferable. When the divalent linking group represented by $R^2$ includes at least one hydroxyl group, in particular, in a case where the protective layer to which the lubricant is applied is formed of carbon or nitrogen-containing carbon, adhesion between the protective layer and the lubricating layer including the fluorine-containing ether compound is further improved.

When the divalent linking group represented by $R^2$ includes one or more polar groups, the number of polar groups in the linking group is not particularly limited, and may be one or plural. The number of polar groups in the linking group is preferably 4 or less in order to prevent the number-average molecular weight of the fluorine-containing ether compound from becoming too large.

In Formula (1), the divalent linking group represented by $R^2$ preferably has 1 to 20 carbon atoms. When the number of carbon atoms is 20 or less, the number-average molecular weight of the fluorine-containing ether compound can be prevented from becoming too large. The number of carbon atoms in the linking group is more preferably 3 to 12.

Specifically, $R^2$ in Formula (1) is preferably represented by Formula (6).

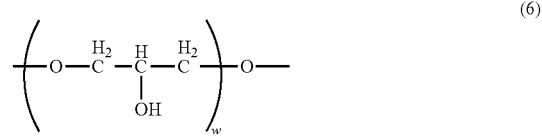

(6)

(In Formula (6), w represents 1 to 4.)

In Formula (6), in a case where w is 1 or more, the divalent linking group represented by $R^2$ includes one or more hydroxyl groups, and the adhesion between the protective layer and the lubricating layer becomes more favorable, which is preferable. In addition, in a case where w is 4 or less, the number-average molecular weight of the fluorine-containing ether compound can be prevented from becoming too large, which is preferable. w is more preferably 1 to 2.

$R^2$ in Formula (1) may also be —O— because a fluorine-containing ether compound is easily synthesized.

Specifically, it is preferable that the fluorine-containing ether compound of the present embodiment be any one of compounds represented by Formulas (A) to (U). Since m and n in Formulas (A) to (N) and (P) to (U) and m in Formula (O) are values showing an average polymerization degree, these are not necessarily an integer.

In the compound represented by Formulas (A) to (D), $R^1$ is an alkyl group having no substituent, $R^2$ is represented by Formula (6) where w is 1, $R^3$ is represented by Formula (3), and $R^4$ is represented by Formula (2-1).

In the compound represented by Formulas (E) to (G), $R^1$ is an alkyl group having a fluoro group, $R^2$ is represented by Formula (6) where w is 1, $R^3$ is represented by Formula (3), and $R^4$ is represented by Formula (2-1).

In the compound represented by Formula (H), $R^1$ is an alkyl group having a fluoro group, $R^2$ is ethereal bond (—O—), $R^3$ is represented by Formula (3), and $R^4$ is represented by Formula (2-1).

In the compound represented by Formula (I), $R^1$ is an ethyl group, $R^2$ is represented by Formula (6) where w is 1, $R^3$ is represented by Formula (3), and $R^4$ is represented by Formula (2-4).

In the compound represented by Formula (J), $R^1$ is an alkyl group having a fluoro group, $R^2$ is represented by Formula (6) where w is 1, $R^3$ is represented by Formula (3), and $R^4$ is represented by Formula (2-4).

In the compound represented by Formula (K), $R^1$ is an ethyl group, $R^2$ is represented by Formula (6) where w is 1, $R^3$ is represented by Formula (3), and $R^4$ is represented by Formula (2-2).

In the compound represented by Formula (L), $R^1$ is an alkyl group having a fluoro group, $R^2$ is represented by Formula (6) where w is 1, $R^3$ is represented by Formula (3), and $R^4$ is represented by Formula (2-2).

In the compound represented by Formula (M), $R^1$ is an ethyl group, $R^2$ is represented by Formula (6) where w is 1, $R^3$ is represented by Formula (3), and $R^4$ is represented by Formula (2-3).

In the compound represented by Formula (N), $R^1$ is an alkyl group having a fluoro group, $R^2$ is represented by Formula (6) where w is 1, $R^3$ is represented by Formula (3), and $R^4$ is represented by Formula (2-3).

In the compound represented by Formula (O), $R^1$ is an alkyl group having a fluoro group, $R^2$ is represented by Formula (6) where w is 1, $R^3$ is represented by Formula (5), and $R^4$ is represented by Formula (2-1).

In the compound represented by Formula (P), $R^1$ is an alkyl group having an alkoxy group, $R^2$ is represented by Formula (6), $R^3$ is represented by Formula (3), and $R^4$ is represented by Formula (2-1).

In the compound represented by Formula (Q), $R^1$ is an alkyl group having a fluoro group and an alkoxy group, $R^2$ is represented by Formula (6), $R^3$ is represented by Formula (3), and $R^4$ is represented by Formula (2-1).

In the compound represented by Formula (R), $R^1$ is an alkyl group having a fluoro group and an alkoxy group, $R^2$ is represented by Formula (6), $R^3$ is represented by Formula (3), and $R^4$ is represented by Formula (2-1).

In the compound represented by Formula (S), $R^1$ is an alkyl group having a fluoro group and a hydroxyl group, $R^2$ is represented by Formula (6), $R^3$ is represented by Formula (3), and $R^4$ is represented by Formula (2-1).

In the compound represented by Formula (T), $R^1$ is an alkyl group having a fluoro group and an alkoxy group, $R^2$ is represented by Formula (6), $R^3$ is represented by Formula (3), and $R^4$ is represented by Formula (2-1).

In the compound represented by Formula (U), $R^1$ is an alkyl group having a fluoro group and an alkoxy group, $R^2$ is represented by Formula (6), $R^3$ is represented by Formula (3), and $R^4$ is represented by Formula (2-1).

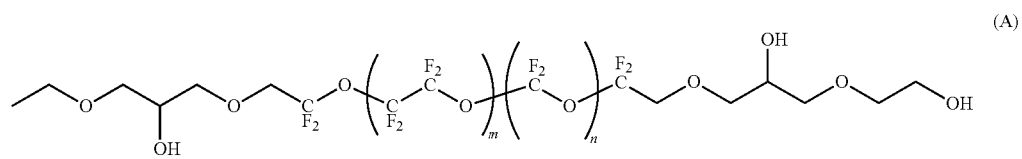

(A)

(In Formula (A), m and n represent average polymerization degrees, m represents 1 to 30, and n represents 0 to 30.)

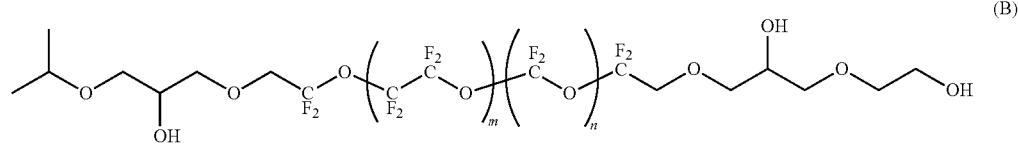

(B)

(In Formula (B), m and n represent average polymerization degrees, m represents 1 to 30, and n represents 0 to 30.)

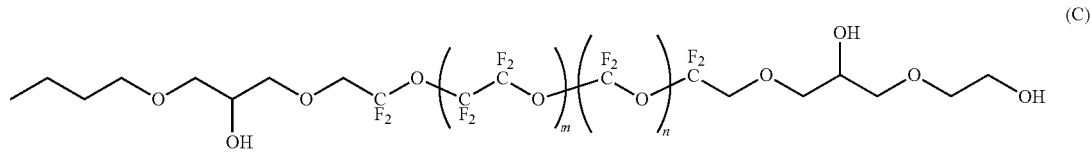

(C)

(In Formula (C), m and n represent average polymerization degrees, m represents 1 to 30, and n represents 0 to 30.)

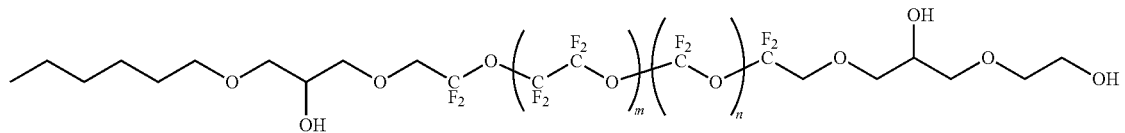
(D)

(In Formula (D), m and n represent average polymerization degrees, m represents 1 to 30, and n represents 0 to 30.)

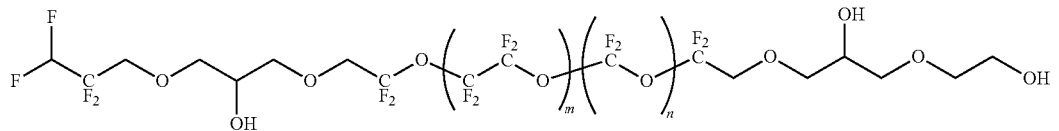
(E)

(In Formula (E), m and n represent average polymerization degrees, m represents 1 to 30, and n represents 0 to 30.)

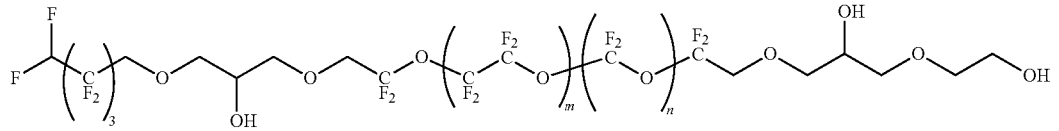
(F)

(In Formula (F), m and n represent average polymerization degrees, m represents 1 to 30, and n represents 0 to 30.)

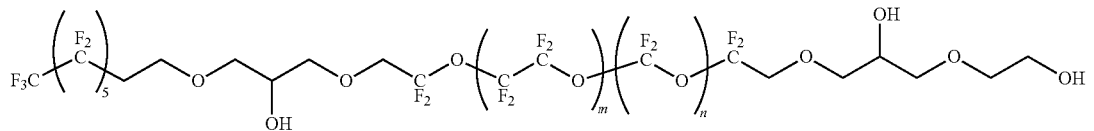
(G)

(In Formula (G), m and n represent average polymerization degrees, m represents 1 to 30, and n represents 0 to 30.)

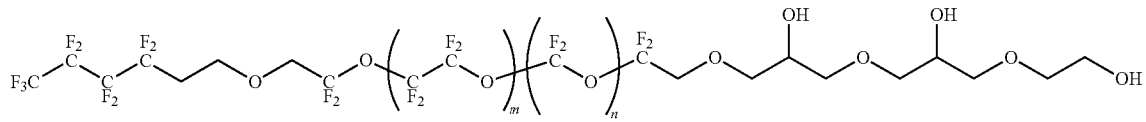
(H)

(In Formula (H), m and n represent average polymerization degrees, m represents 1 to 30, and n represents 0 to 30.)

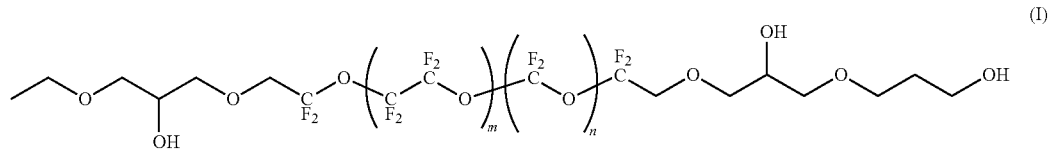

(I)

(In Formula (I), m and n represent average polymerization degrees, m represents 1 to 30, and n represents 0 to 30.)

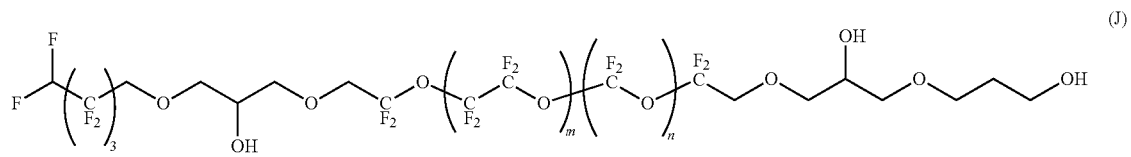

(J)

(In Formula (J), m and n represent average polymerization degrees, m represents 1 to 30, and n represents 0 to 30.)

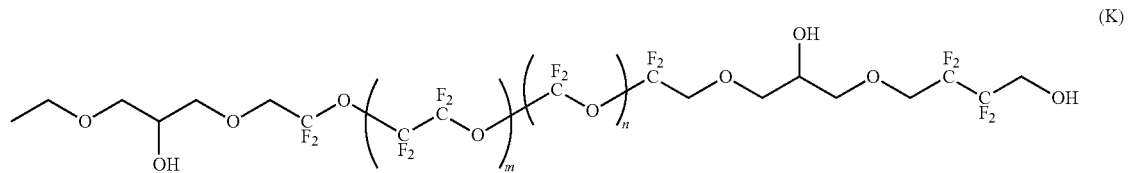

(K)

(In Formula (K), m and n represent average polymerization degrees, m represents 1 to 30, and n represents 0 to 30.)

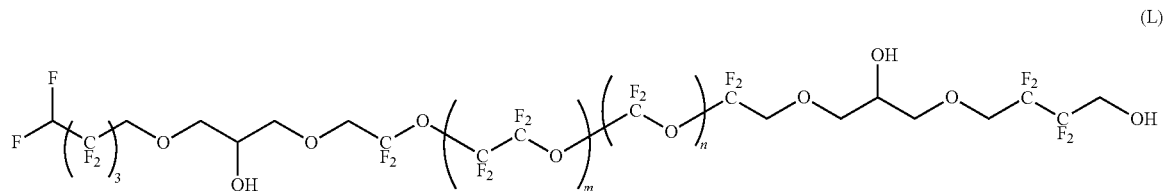

(L)

(In Formula (L), m and n represent average polymerization degrees, m represents 1 to 30, and n represents 0 to 30.)

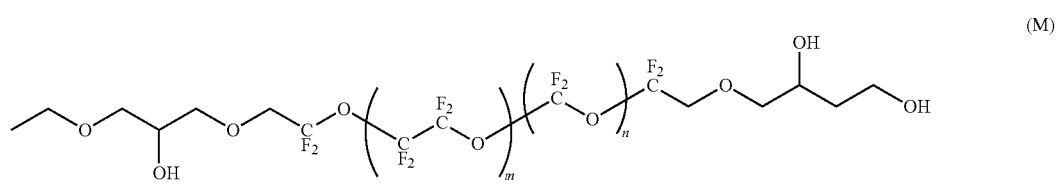

(M)

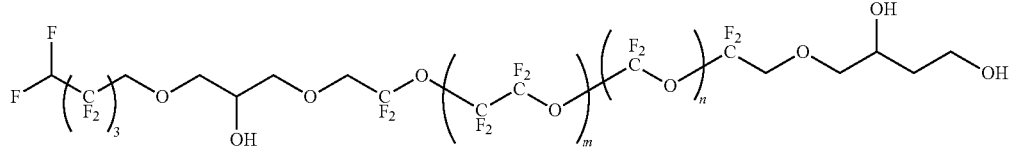
(In Formula (M), m and n represent average polymerization degrees, m represents 1 to 30, and n represents 0 to 30.)
(In Formula (N), m and n represent average polymerization degrees, m represents 1 to 30, and n represents 0 to 30.)
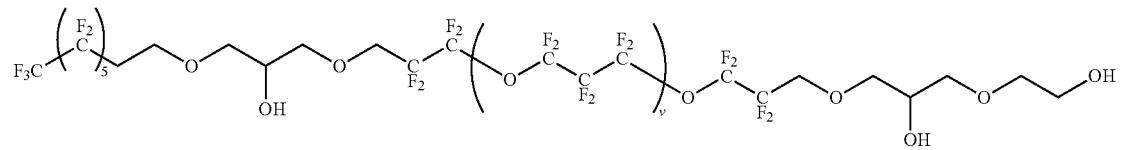
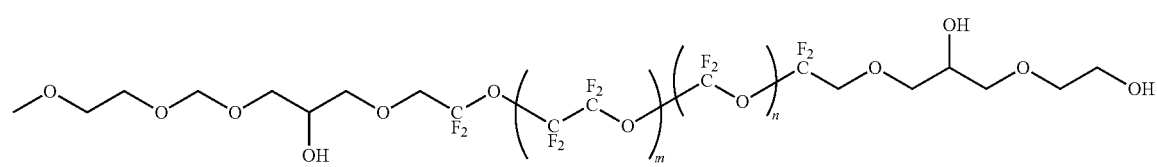
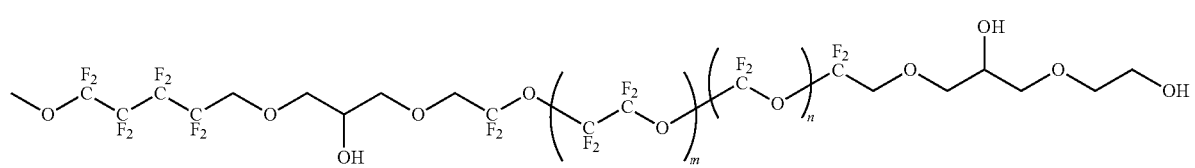
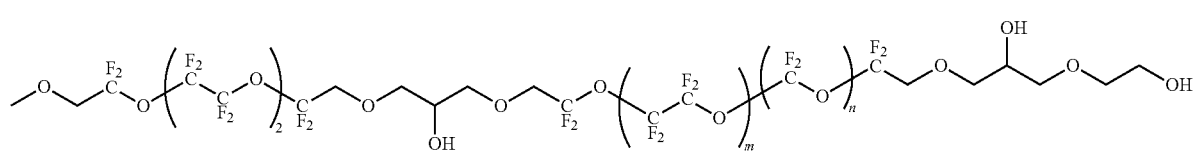
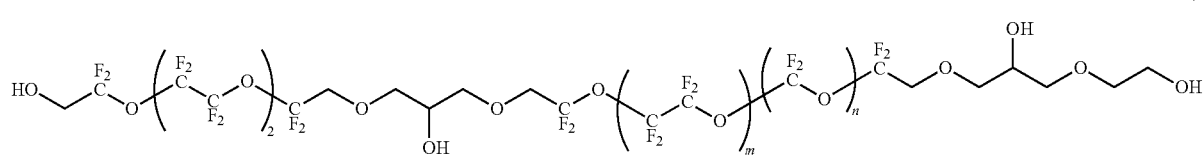
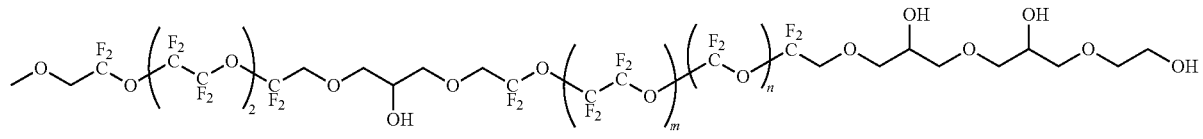
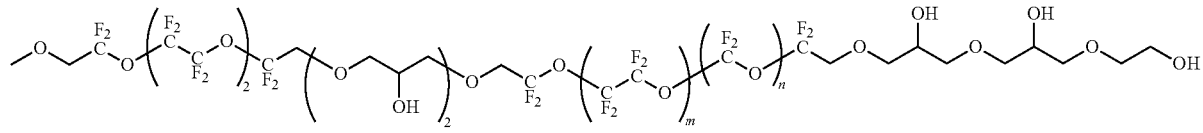

(In Formula (O), v represents an average polymerization degree and v represents 1 to 30.)

(In Formula (P), m and n represent average polymerization degrees, m represents 1 to 30, and n represents 0 to 30.)

(In Formula (Q), m and n represent average polymerization degrees, m represents 1 to 30, and n represents 0 to 30.)

(In Formula (R), m and n represent average polymerization degrees, m represents 1 to 30, and n represents 0 to 30.)

(In Formula (S), m and n represent average polymerization degrees, m represents 1 to 30, and n represents 0 to 30.)

(In Formula (T), m and n represent average polymerization degrees, m represents 1 to 30, and n represents 0 to 30.)

(In Formula (U), m and n represent average polymerization degrees, m represents 1 to 30, and n represents 0 to 30.)

When the compound represented by Formula (1) is any one of the compounds represented by the Formulas (A) to (U), a raw material is easily available, and it is possible to form a lubricating layer in which excellent chemical resistance and wear resistance are obtained even when a thickness thereof is reduced, which are preferable.

In the fluorine-containing ether compound of the present embodiment, a number-average molecular weight (Mn) is preferably in a range of 500 to 10000. When the number-average molecular weight is 500 or more, the lubricant including the fluorine-containing ether compound of the present embodiment is less likely to evaporate, and it is possible to prevent the lubricant from evaporating and transferring to a magnetic head. The number-average molecular weight of the fluorine-containing ether compound is more preferably 1000 or more. In addition, when the number-average molecular weight is 10000 or less, the viscosity of the fluorine-containing ether compound is appropriate, and when applying a lubricant including the compound, a lubricating layer having a reduced thickness can be easily formed. The number-average molecular weight of the fluorine-containing ether compound is preferably 3000 or less, from the viewpoint that viscosity for easy handling is obtained in a case of being applied to a lubricant.

The number-average molecular weight (Mn) of the fluorine-containing ether compound is a value measured by $^1$H-NMR and $^{19}$F-NMR using AVANCE III 400 manufactured by Bruker Biospin. In measurement of nuclear magnetic resonance (NMR), a sample was diluted in a single or mixed solvent such as hexafluorobenzene, d-acetone, and d-tetrahydrofuran, to be used for the measurement. For the standard of $^{19}$F-NMR chemical shift, the peak of hexafluorobenzene was set to −164.7 ppm. For the standard of $^1$H-NMR chemical shift, the peak of acetone was set to 2.2 ppm.

"Production Method"

A production method of the fluorine-containing ether compound of the present embodiment is not particularly limited, and the fluorine-containing ether compound can be produced using a known production method of the related art. The fluorine-containing ether compound of the present embodiment can be produced, for example, using the following production method.

First, a fluorine-based compound including hydroxymethyl groups (—CH$_2$OH) respectively at both ends of a perfluoropolyether chain corresponding to R$^3$ in Formula (1) is prepared.

Next, a hydroxyl group of the hydroxymethyl group at one end of the fluorine-based compound is substituted with a group represented by R$^1$-R$^2$— in Formula (1) (first reaction). Thereafter, the hydroxyl group of the hydroxymethyl group at the other end is substituted with an end group represented by —R$^4$ in Formula (1) (second reaction).

The first reaction and the second reaction can be performed using a method known in the related art, and can be appropriately determined according to types of R$^1$, R$^2$, and R$^4$ in Formula (1). In addition, either the first reaction or the second reaction may be performed first.

For example, in a case of producing a fluorine-containing ether compound in which R$^2$ is represented by Formula (6) where w is 1, in general, in the first reaction, a fluorine-based compound and an epoxy compound having a glycidyl group are reacted to substitute a hydroxyl group of the fluorine-based compound with a group represented by R$^1$-R$^2$— in Formula (1). In this case, in the produced fluorine-containing ether compound, an ethereal oxygen of R$^2$ bonded to R$^1$ is an oxygen atom to which the glycidyl group was bonded in the epoxy compound used in the first reaction. For example, in a case where the epoxy compound used in the first reaction is a compound represented by Formula (22), the oxygen bonded to —CH$_2$ of the glycidyl group becomes the ethereal oxygen of R$^2$ bonded to R$^1$.

A compound represented by Formula (1) is obtained by using the method as above.

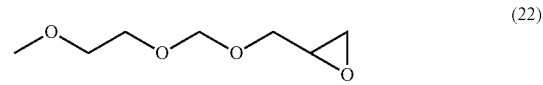

(22)

In the present embodiment, in a case of producing a fluorine-containing ether compound in which R$^2$ is represented by Formula (6), it is preferable to use an epoxy compound for the production. The epoxy compound can be purchased commercially, and may also be synthesized using an alcohol having a structure corresponding to the alkyl group represented by R$^1$ that may have a substituent in the fluorine-containing ether compound and epichlorohydrin or epibromohydrin.

The fluorine-containing ether compound of the present embodiment is a compound represented by Formula (1). Therefore, when the lubricating layer is formed on the protective layer using a lubricant including the compound, the surface of the protective layer is covered with the PFPE chain represented by R$^3$ in Formula (1), and frictional force between the magnetic head and the protective layer is reduced. In addition, in the lubricating layer formed using the lubricant including the fluorine-containing ether compound of the present embodiment, excellent wear resistance is obtained by an intermolecular interaction of the alkyl group represented by R$^1$ that may have a substituent and/or an interaction between the alkyl group and the protective layer.

In addition, in the fluorine-containing ether compound of the present embodiment, the PFPE chain is closely attached onto the protective layer by bonding between the two or three polar groups of R$^4$ linked to the PFPE chain and the protective layer. Therefore, according to the fluorine-containing ether compound of the present embodiment, the lubricating layer and the protective layer are firmly bonded, and a lubricating layer having excellent chemical resistance and wear resistance can be obtained.

[Lubricant for Magnetic Recording Medium]

The lubricant for a magnetic recording medium of the present embodiment includes the fluorine-containing ether compound represented by Formula (1).

The lubricant of the present embodiment can be used by being mixed with a known material used as a lubricant material as needed, within a range not impairing the characteristics obtained by including the fluorine-containing ether compound represented by Formula (1).

Specific examples of the known material include FOMBLIN (registered trademark) ZDIAC, FOMBLIN ZDEAL, and FOMBLIN AM-2001 (all manufactured by Solvey Solexis), and Moresco A20H (manufactured by Moresco). The number-average molecular weight of the known material used by being mixed with the lubricant of the present embodiment is preferably 1000 to 10000.

In a case where the lubricant of the present embodiment includes other materials in addition to the fluorine-containing ether compound represented by Formula (1), a content of the fluorine-containing ether compound represented by Formula (1) in the lubricant of the present embodiment is preferably 50% by mass or more, and more preferably 70% by mass or more. A upper limit can be optionally selected. For example, the upper limit may be 99% by mass or less, 95% by mass or less, 90% by mass or less, or 85% by mass or less.

Since the lubricant of the present embodiment includes the fluorine-containing ether compound represented by Formula (1), even when the thickness is reduced, the surface of the protective layer can be covered with high coverage, and it is possible to form a lubricating layer with excellent adhesion to the protective layer. Therefore, according to the lubricant of the present embodiment, the lubricating layer having excellent chemical resistance and wear resistance can be obtained, even when the thickness is reduced.

In addition, since the lubricant of the present embodiment includes the fluorine-containing ether compound represented by Formula (1), the fluorine-containing ether compound in the lubricant layer not adhering (adsorbing) to the protective layer is less likely to aggregate. Accordingly, it is possible to prevent the fluorine-containing ether compound from aggregating and adhering to a magnetic head as foreign substance (smear), and pickup is suppressed.

In addition, since the lubricant of the present embodiment includes a fluorine-containing ether compound represented by Formula (1), a lubricating layer having excellent wear resistance can be obtained by an intermolecular interaction of the alkyl group represented by $R^1$ that may have a substituent in Formula (1), and/or an interaction between the alkyl group and the protective layer.

[Magnetic Recording Medium]

The magnetic recording medium of the present embodiment is obtained by providing at least a magnetic layer, a protective layer, and a lubricating layer in this order on a substrate.

In the magnetic recording medium of the present embodiment, one or more base layers can be provided between the substrate and the magnetic layer, as needed. In addition, an adhesion layer and/or a soft magnetic layer can be provided between the base layer and the substrate.

FIG. 1 is a schematic sectional view showing a preferred embodiment of the magnetic recording medium according to the present invention.

A magnetic recording medium 10 of the present embodiment has a structure in which an adhesion layer 12, a soft magnetic layer 13, a first base layer 14, a second base layer 15, a magnetic layer 16, a protective layer 17, and a lubricating layer 18 are provided in this order on a substrate 11.

"Substrate"

The substrate 11 can be optionally selected. For example, a nonmagnetic substrate or the like in which a film formed of NiP or an NiP alloy is formed on a base substrate formed of metal or alloy material such as Al or an Al alloy can be preferably used as a base material 11.

In addition, as the substrate 11, a nonmagnetic substrate formed of a nonmetallic material such as glass, ceramics, silicon, silicon carbide, carbon, and resin may be used. A nonmagnetic substrate in which a film of NiP or an NiP alloy is formed on a base substrate formed of the nonmetallic materials may also be used as the substrate 11.

"Adhesion Layer"

The adhesion layer 12 prevents corrosion of the substrate 11 from progressing, which occurs in a case where the substrate 11 and the soft magnetic layer 13 provided on the adhesion layer 12 are disposed in contact with each other.

Material used for the adhesion layer 12 can be optionally selected. For example, a material can be appropriately selected from, Cr, a Cr alloy, Ti, a Ti alloy, CrTi, NiAl, an AlRu alloy, and the like. The adhesion layer 12 can be formed, for example, by a sputtering method.

"Soft Magnetic Layer"

The soft magnetic layer 13 can be optionally selected, and the soft magnetic layer 13 preferably has a structure in which a first soft magnetic film, an intermediate layer formed of a Ru film, and a second soft magnetic film are laminated in this order. That is, the soft magnetic layer 13 preferably has a structure in which the intermediate layer formed of the Ru film is sandwiched between the two soft magnetic films to couple the soft magnetic films above and below the intermediate layer by anti-ferro coupling (AFC).

Examples of materials of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. Accordingly, amorphization of the first soft magnetic film and the second soft magnetic film is promoted, an orientation of the first base layer (seed layer) can be improved, and flying height of a magnetic head can be reduced.

The soft magnetic layer 13 can be formed, for example, by a sputtering method.

"First Base Layer"

The first base layer 14 is a layer for controlling the orientation or crystal size of the second base layer 15 and the magnetic layer 16 provided thereon.

Examples of the first base layer 14 include a Cr layer, a Ta layer, a Ru layer, or an alloy layer of CrMo, CoW, CrW, CrV, or CrTi.

The first base layer 14 can be formed, for example, by a sputtering method.

"Second Base Layer"

The second base layer 15 is a layer that controls the orientation of the magnetic layer 16 to be favorable. The second base layer 15 can be optionally selected, and the second base layer 15 is preferably a layer formed of Ru or a Ru alloy.

The second base layer 15 may be a layer formed by a single layer or may be formed of a plurality of layers. In a case where the second base layer 15 is formed of a plurality of layers, all the layers may be formed of the same material, or at least one layer may be formed of a different material.

The second base layer 15 can be formed, for example, by a sputtering method.

"Magnetic Layer"

The magnetic layer 16 is formed of a magnetic film in which an easy axis of magnetization is oriented in a direction perpendicular or horizontal to a substrate surface. The magnetic layer 16 can be optionally selected, and the magnetic layer 16 is preferably a layer including Co and Pt, and in order to further improve an SNR characteristic, it may be a layer including an oxide, Cr, B, Cu, Ta, Zr, or the like.

Examples of the oxide included in the magnetic layer 16 include $SiO_2$, SiO, $Cr_2O_3$, CoO, $Ta_2O_3$, and $TiO_2$.

The magnetic layer 16 may be a layer formed of a single layer or may be formed of a plurality of magnetic layers including materials having a different composition.

For example, in a case where the magnetic layer 16 is formed of three layers of a first magnetic layer, a second magnetic layer, and a third magnetic layer, which are laminated in this order from the bottom, the first magnetic layer preferably has a granular structure that includes a material containing Co, Cr, and Pt, and further containing an oxide. As the oxide included in the first magnetic layer, for example, oxides of Cr, Si, Ta, Al, Ti, Mg, Co, and the like are preferably used. Among these, in particular, $TiO_2$, $Cr_2O_3$, $SiO_2$, and the like can be suitably used. In addition, it is preferable that the first magnetic layer includes a complex oxide obtained by adding two or more kinds of oxides. Among these, in particular, $Cr_2O_3$—$SiO_2$, $Cr_2O_3$—$TiO_2$, and $SiO_2$—$TiO_2$ can be suitably used.

The first magnetic layer can include one or more elements selected from B, Ta, Mo, Cu, Nd, W, Nb, Sm, Tb, Ru, and Re, in addition to Co, Cr, Pt, and an oxide.

For the second magnetic layer, the same material as the first magnetic layer can be used. The second magnetic layer preferably has a granular structure.

The third magnetic layer preferably has a non-granular structure including a material that includes Co, Cr, and Pt and does not include an oxide. The third magnetic layer can include one or more elements selected from B, Ta, Mo, Cu, Nd, W, Nb, Sm, Tb, Ru, Re, and Mn, in addition to Co, Cr, and Pt.

In a case where the magnetic layer 16 is formed of a plurality of magnetic layers, it is preferable to provide a non-magnetic layer between adjacent magnetic layers. In a case where the magnetic layer 16 is formed of three layers that are the first magnetic layer, the second magnetic layer, and the third magnetic layer, a nonmagnetic layer is preferably provided between the first magnetic layer and the second magnetic layer and between the second magnetic layer and the third magnetic layer.

For the nonmagnetic layer provided between the adjacent magnetic layers of the magnetic layer 16, for example, Ru, a Ru alloy, a CoCr alloy, and CoCrX1 alloy (X1 represents one or more elements selected from Pt, Ta, Zr, Re, Ru, Cu, Nb, Ni, Mn, Ge, Si, O, N, W, Mo, Ti, V, and B) can be suitably used.

For the nonmagnetic layer provided between the adjacent magnetic layers of the magnetic layer 16, it is preferable to use an alloy material including an oxide, a metal nitride, or a metal carbide. Specifically, as the oxide, for example, $SiO_2$, $Al_2O_3$, $Ta_2O_5$, $Cr_2O_3$, MgO, $Y_2O_3$, and $TiO_2$ can be used. As the metal nitride, for example, AlN, $Si_3N_4$, TaN, and CrN can be used. As the metal carbide, for example, TaC, BC, and SiC can be used.

The nonmagnetic layer can be formed, for example, by a sputtering method.

In order to realize higher recording density, the magnetic layer 16 is preferably a magnetic layer for perpendicular magnetic recording in which the easy axis of magnetization is perpendicular to the substrate surface. The magnetic layer 16 may be a magnetic layer for in-plane magnetic recording.

The magnetic layer 16 may be formed by a vapor deposition method, an ion beam sputtering method, a magnetron sputtering method, and any known method of the related art. The magnetic layer 16 is usually formed by the sputtering method.

"Protective Layer"

The protective layer 17 protects the magnetic layer 16. The protective layer 17 may be a layer formed of a single layer or may be formed of a plurality of layers. Examples of the material for the protective layer 17 include carbon, nitrogen-containing carbon, and silicon carbide.

As the protective layer 17, a carbon-based protective layer can be preferably used, and an amorphous carbon protective layer is particularly preferable. It is preferable that the protective layer 17 be the carbon-based protective layer, from the viewpoint that the interaction with the polar group (particularly, a hydroxyl group) included in the fluorine-containing ether compound in the lubricating layer 18 is further enhanced.

The adhesion force between the carbon-based protective layer and the lubricating layer 18 can be controlled by using hydrogenated carbon and/or nitrogenated carbon as the carbon-based protective layer and adjusting a hydrogen content and/or a nitrogen content in the carbon-based protective layer. The hydrogen content in the carbon-based protective layer is preferably 3 to 20 atomic % as measured by hydrogen forward scattering (HFS). In addition, the nitrogen content in the carbon-based protective layer is preferably 4 to 15 atomic % as measured by X-ray photoelectron spectroscopy (XPS).

Hydrogen and/or nitrogen included in the carbon-based protective layer need not be uniformly contained throughout the carbon-based protective layer. The carbon-based protective layer is preferably, for example, a composition gradient layer in which the nitrogen is contained on the lubricating layer 18 side of the protective layer 17 and the hydrogen is contained on the magnetic layer 16 side of the protective layer 17. In this case, the adhesion force between the magnetic layer 16 and the carbon-based protective layer and between the lubricating layer 18 and the carbon-based protective layer is further enhanced.

A film thickness of the protective layer 17 is preferably 1 nm to 7 nm. When the film thickness of the protective layer 17 is 1 nm or more, performance as the protective layer 17 is sufficiently obtained. It is preferable that the film thickness of the protective layer 17 be 7 nm or less, from the viewpoint of thinning the protective layer 17.

As the film forming method of the protective layer 17, a sputtering method using a target material containing carbon, a chemical vapor deposition (CVD) method using a hydrocarbon raw material such as ethylene or toluene, an ion beam deposition (IBD) method, or the like can be used.

In a case of forming the carbon-based protective layer as the protective layer 17, a film can be formed for example, by a DC magnetron sputtering method. In particular, in a case of forming the carbon-based protective layer as the protective layer 17, it is preferable to form an amorphous carbon protective layer by a plasma CVD method. The amorphous carbon protective layer formed by the plasma CVD method has a uniform surface and small roughness.

"Lubricating Layer"

The lubricating layer 18 prevents the magnetic recording medium 10 from being contaminated. In addition, the lubricating layer 18 reduces frictional force of a magnetic head of a magnetic recording and reproducing apparatus sliding on the magnetic recording medium 10, and improves durability of the magnetic recording medium 10.

As shown in FIG. 1, the lubricating layer 18 is preferably formed on and in contact with the protective layer 17. The lubricating layer 18 includes the fluorine-containing ether compound described above.

In a case where the protective layer 17 disposed under the lubricating layer 18 is the carbon-based protective layer, in particular, the lubricating layer 18 is bonded to the protective layer 17 with high bonding strength. As a result, even when the thickness of the lubricating layer 18 is reduced, the magnetic recording medium 10 in which the surface of the protective layer 17 is covered with high coverage is easily obtained, and it is possible to effectively prevent the surface of the magnetic recording medium 10 from being contaminated.

A predetermined average film thickness of the lubricating layer 18 can be selected, and the average film thickness is preferably 0.5 nm (5 Å) to 3 nm (30 Å), and more preferably 0.5 nm (5 Å) to 2 nm (20 Å). When the average film thickness of the lubricating layer 18 is 0.5 nm or more, the lubricating layer 18 is formed in a uniform film thickness without being in an island form or a mesh form. Therefore, the surface of the protective layer 17 can be covered with high coverage, by the lubricating layer 18. In addition, when setting the average film thickness of the lubricating layer 18 to 3 nm or less, the lubricating layer 18 can be sufficiently thinned, and the flying height of the magnetic head can be sufficiently reduced.

In a case where the surface of the protective layer 17 is not covered with the lubricating layer 18 with a sufficiently high coverage, an environmental substance adsorbed on the surface of the magnetic recording medium 10 passes through a gap in the lubricating layer 18 and enters under the lubricating layer 18. The environmental substance that enters a lower layer of the lubricating layer 18 is adsorbed and bonded with the protective layer 17 to generate a contaminant. During magnetic recording and reproducing, the contaminant (aggregation component) adheres (transfers) to a magnetic head as a smear to damage the magnetic head or degrade a magnetic recording and reproducing characteristic of the magnetic recording and reproducing apparatus.

Examples of the environmental substance that generates the contaminant include a siloxane compound (cyclic siloxane or linear siloxane), an ionic compound, hydrocarbon having relatively high molecular weight such as octacosane, and a plasticizer such as dioctyl phthalate. Examples of a metal ion contained in the ionic impurities include a sodium ion and a potassium ion. Examples of an inorganic ion contained in the ionic impurities include a chlorine ion, a bromine ion, a nitrate ion, a sulfate ion, and an ammonium ion. Examples of an organic ion contained in the ionic impurities include an oxalate ion and a formate ion.

"Method of Forming Lubricating Layer"

Examples of a method of forming the lubricating layer 18 include a method in which a magnetic recording medium in the middle of production, at which each layer up to the protective layer 17 is formed on the substrate 11, is prepared, and the lubricating layer-forming solution is applied onto the protective layer 17 and dried.

The lubricating layer-forming solution is obtained by dispersing and dissolving the lubricant for a magnetic recording medium of the embodiment in a solvent as needed to set a viscosity and concentration suitable for a coating method.

Examples of the solvent used for the lubricating layer-forming solution include a fluorinated solvent such as Vertrel (registered trademark) XF (trade name, manufactured by Du Pont-Mitsui Fluorochemicals Co., Ltd.).

The coating method of the lubricating layer-forming solution is not specifically limited, and examples thereof include a spin coat method, a spray method, a paper coat method, and a dip method.

In a case of using the dip method, for example, the following method can be used. First, the substrate 11 in which each layer up to the protective layer 17 is formed is immersed in the lubricating layer-forming solution contained in an immersion tank of a dip coating apparatus. Then, the substrate 11 is pulled up from the immersion tank at a predetermined speed.

According to this, the lubricating layer-forming solution is applied to the surface on the protective layer 17 of the substrate 11.

When using the dip method, the lubricating layer-forming solution can be uniformly applied to the surface of the protective layer 17, and the lubricating layer 18 can be formed on the protective layer 17 with uniform film thickness.

In the present embodiment, it is preferable to carry out heat treatment on the substrate 11 on which the lubricating layer 18 is formed. By applying the heat treatment, the adhesion between the lubricating layer 18 and the protective layer 17 improves, and the adhesion force between the lubricating layer 18 and the protective layer 17 improves.

A heat treatment temperature is preferably set to 100° C. to 180° C. When the heat treatment temperature is 100° C. or higher, an effect of improving the adhesion between the lubricating layer 18 and the protective layer 17 is sufficiently obtained. In addition, when the heat treatment temperature is set to be 180° C. or lower, it is possible to prevent the lubricating layer 18 from being thermally decomposed. Heat treatment time is preferably 10 to 120 minutes.

The magnetic recording medium 10 of the present embodiment is obtained by providing at least the magnetic layer 16, the protective layer 17, and the lubricating layer 18 in this order on the substrate 11. In the magnetic recording medium 10 of the present embodiment, the lubricating layer 18 including the fluorine-containing ether compound described above is formed on and in contact with the protective layer 17. The surface of the protective layer 17 is covered with the lubricating layer 18 with a high coverage, even when the thickness of the lubricating layer is reduced.

Accordingly, in the magnetic recording medium 10 of the present embodiment, the environmental substance that generates the contaminant such as ionic impurities are prevented from entering the gap in the lubricating layer 18. Therefore, the magnetic recording medium 10 of the present embodiment has few contaminants present on the surface. In addition, in the magnetic recording medium 10 of the present embodiment, the lubricating layer 18 is less likely to generate foreign substance (smear) and can suppress pickup. In addition, in the magnetic recording medium 10 of the present embodiment, the lubricating layer 18 has excellent chemical resistance and wear resistance. Therefore, the magnetic recording medium 10 of the present embodiment has excellent reliability and durability.

EXAMPLES

Hereinafter, the present invention will be further specifically described, using Examples and Comparative Examples. The present invention is not limited to only the following Examples.

Production of Lubricant

Example 1

According to a method shown below, a compound represented by Formula (A) was produced.

20.0 g of a compound (number-average molecular weight of 1000 and molecular weight distribution of 1.1) represented by $HOCH_2CF_2O(CF_2CF_2O)_{m1}(CF_2O)_{n1}CF_2CH_2OH$ (in the formula, m1 indicating an average polymerization degree represents 4.5 and n1 indicating an average polymerization degree represents 4.5) and 1.22 g of a compound represented by Formula (7), and 12 mL of t-butanol were charged into a 100-mL eggplant flask under a nitrogen gas atmosphere, and stirred at room temperature to be homogeneous. 0.674 g of potassium tert-butoxide was added to the homogeneous solution, and stirred and reacted at 70° C. for 8 hours to obtain a reaction product.

The obtained reaction product was cooled to 25° C. and neutralized with 0.5 mol/L hydrochloric acid, and then extracted with Vertrel XF (manufactured by Du Pont-Mitsui Fluorochemicals Co., Ltd.) (hereinafter, Vertrel XF), and the organic layer was washed with water. The organic layer was dehydrated with anhydrous sodium sulfate and the desiccant was filtered off. Thereafter, the filtrate was concentrated. The residue was purified by silica gel column chromatography to obtain 8.82 g of a compound represented by Formula (8) as an intermediate.

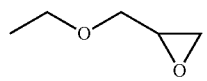

(7)

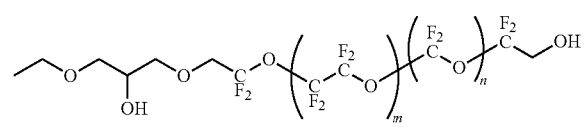

(8)

(In Formula (8), m indicating an average polymerization degree is 4.5 and n indicating an average polymerization degree is 4.5.)

5.51 g of the compound represented by Formula (8), 1.21 g of the compound represented by Formula (9), and 50 mL of t-butanol were charged into a 200-mL eggplant flask under a nitrogen gas atmosphere, and stirred at room temperature to be homogeneous. 0.168 g of potassium tert-butoxide was added to the homogeneous solution, and stirred at 70° C. for 16 hours to be reacted.

The compound represented by Formula (9) was synthesized by oxidizing a compound in which the hydroxyl group of ethylene glycol monoallyl ether is protected with tetrahydropyran.

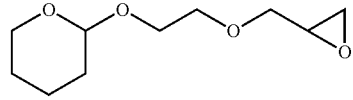

(9)

The solution after the reaction was finished was returned to room temperature, and 20 g of 10% hydrogen chloride-methanol solution was added thereto and stirred at room temperature for 1 hour. The reaction solution was transferred to a beaker containing 70 mL of 8% aqueous sodium bicarbonate, and extracted twice with 200 mL of ethyl acetate. The organic layer was washed with water and dehydrated with anhydrous sodium sulfate, and the desiccant was filtered off. Thereafter, the filtrate was concentrated. The residue was purified by silica gel column chromatography to obtain 3.66 g of Compound (A).

$^1$H-NMR measurement of the obtained Compound (A) was conducted, and a structure was identified from the following results.

Compound (A); $^1$H-NMR ($CD_3COCD_3$);

δ [ppm] 0.90 to 1.20 (3H), 3.55 to 4.20 (20H)

Example 2

3.74 g of Compound (C) was obtained by performing the same operation as in Example 1, except that 1.56 g of a compound represented by Formula (10) was used instead of the compound represented by Formula (7).

$^1$H-NMR measurement of the obtained Compound (C) was conducted, and a structure was identified from the following results.

Compound (C); $^1$H-NMR ($CD_3COCD_3$);

δ [ppm] 0.90 to 1.20 (3H), 1.60 to 2.00 (4H), 3.55 to 4.20 (20H)

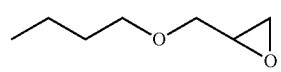

(10)

Example 3

4.22 g of Compound (F) was obtained by way of a compound represented by Formula (12) as an intermediate, by performing the same operation as in Example 1 except that 3.46 g of a compound represented by Formula (11) was used instead of the compound represented by Formula (7).

$^1$H-NMR measurement of the obtained Compound (F) was conducted, and a structure was identified from the following results.

Compound (F); $^1$H-NMR ($CD_3COCD_3$);

δ [ppm] 3.55 to 4.20 (20H) 6.10 (1H)

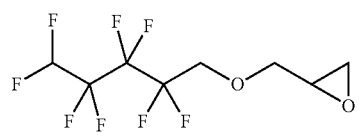

(11)

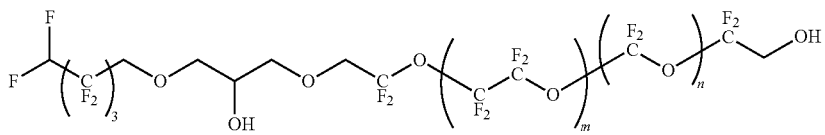
(12)

(In Formula (12), m indicating an average polymerization degree is 4.5 and n indicating an average polymerization degree is 4.5.)

Example 4

4.61 g of Compound (G) was obtained by performing the same operation as in Example 1, except that 5.04 g of a compound represented by Formula (13) was used instead of the compound represented by Formula (7).

$^1$H-NMR measurement of the obtained Compound (G) was conducted, and a structure was identified from the following results.

Compound (G); $^1$H-NMR (CD$_3$COCD$_3$):
δ [ppm]=2.40 (2H), 3.60 to 3.15 (20H)

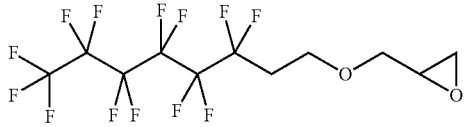
(13)

Example 5

According to a method shown below, a compound represented by Formula (H) was produced.

20.0 g of a compound (number-average molecular weight of 1000 and molecular weight distribution of 1.1) represented by HOCH$_2$CF$_2$O(CF$_2$CF$_2$O)$_{m1}$(CF$_2$O)$_{n1}$CF$_2$CH$_2$OH (in the formula, m1 indicating an average polymerization degree represents 4.5 and n1 indicating an average polymerization degree represents 4.5) and 7.48 g of a compound represented by Formula (14), 8.29 g of potassium carbonate, and 60 mL of acetone were charged into a 300-mL eggplant flask under a nitrogen gas atmosphere, and stirred under reflux for 24 hours to be reacted.

The obtained reaction product was cooled to 25° C., and the acetone was distilled off. The residue was washed with water by adding Vertrel XF, and dehydrated with anhydrous sodium sulfate and the desiccant was filtered off. Thereafter, the filtrate was concentrated. The residue was purified by silica gel column chromatography to obtain 7.52 g of a compound represented by Formula (15) as an intermediate.

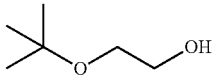
(14)

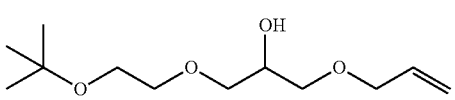
(15)

(In Formula (15), m indicating an average polymerization degree is 4.5 and n indicating an average polymerization degree is 4.5.)

11.82 g of the compound represented by Formula (16), 250 mL of t-butanol, and 11.42 g of allyl glycidyl ether were charged into a 500-mL eggplant flask under a nitrogen gas atmosphere, and stirred to be homogeneous. 3.36 g of potassium tert-butoxide was added to the homogeneous solution, and stirred at 70° C. for 4 hours to be reacted. The obtained reaction product was cooled to 25° C., and t-butanol was distilled off. The residue was washed with water by adding ethyl acetate, and dehydrated with anhydrous sodium sulfate and the desiccant was filtered off. Thereafter, the filtrate was concentrated. The residue was purified by silica gel column chromatography to obtain 9.30 g of a compound represented by Formula (17).

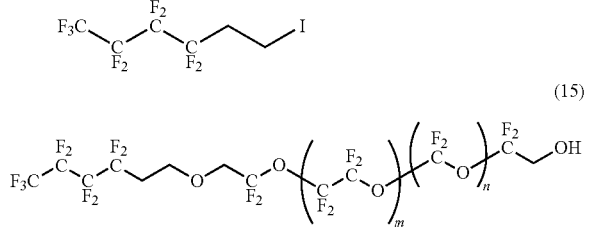
(16)

(17)

9.30 g of the compound represented by Formula (17) and 100 mL of dichloromethane were charged into a 300 mL eggplant flask, 10.0 g of metachloroperbenzoic acid (70% product) was added thereto under ice cooling, and stirred at the same temperature for 1 hour and at room temperature for 12 hours. 10 mL of a saturated aqueous sodium sulfite solution was added to the reaction solution under ice cooling, and was stirred for 30 minutes. The solution was transferred to a separatory funnel, and the organic layer was washed with 5% aqueous sodium bicarbonate solution and then with water, and dehydrated with anhydrous sodium sulfate. The desiccant was filtered off. Thereafter, the filtrate was concentrated. The residue was purified by silica gel column chromatography to obtain 4.97 g of a compound represented by Formula (18).

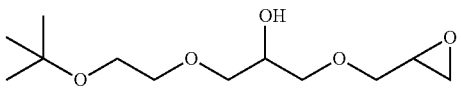
(18)

6.23 g of the compound represented by Formula (15) obtained by the above method, 1.49 g of the compound represented by Formula (18), and 50 mL of t-butanol were charged into a 100-mL eggplant flask under a nitrogen gas atmosphere, and stirred at room temperature to be homogeneous. 0.168 g of potassium tert-butoxide was added to the homogeneous solution, and stirred at 70° C. for 12 hours to be reacted. The obtained reaction product was cooled to 25°

C., neutralized with 0.1 mol/L hydrochloric acid. Thereafter, extraction was performed with Vertrel XF, the organic layer was washed with water and dehydrated with anhydrous sodium sulfate. The desiccant was filtered off. Thereafter, the filtrate was concentrated.

0.75 mL of water and 7.5 mL of trifluoroacetic acid were added to the obtained residue at room temperature, and was stirred at room temperature for 1 hour. Vertrel XF, water, and trifluoroacetic acid were distilled off at 35° C. or lower, and 30 mL of 5% aqueous sodium bicarbonate was added to the obtained residue, followed by extraction with Vertrel XF. The organic layer was washed with water and concentrated. 5 mL of methanol and 14 mL of 1 mol/L sodium hydroxide aqueous solution were added to the obtained residue and stirred at room temperature for 1 hour. Thereafter, methanol was distilled off, extraction was performed with Vertrel XF. The organic layer was washed with 1 mol/L hydrochloric acid and water and dehydrated with anhydrous sodium sulfate. The desiccant was filtered off Thereafter, the filtrate was concentrated. The residue was purified by silica gel column chromatography to obtain 3.30 g of Compound (H).

$^1$H-NMR measurement of the obtained Compound (H) was conducted, and a structure was identified from the following results.

Compound (H); $^1$H-NMR (CD$_3$COCD$_3$);

δ [ppm] 2.40 (2H), 3.60 to 4.20 (20H)

5.00 g of the compound represented by Formula (19), 28 mL of t-butanol, and 3.50 g of propylene glycol were charged into a 100-mL eggplant flask under a nitrogen gas atmosphere, and stirred to be homogeneous. 0.168 g of potassium tert-butoxide was added to the homogeneous solution, and stirred at 70° C. for 6 hours to be reacted. The obtained reaction product was cooled to 25° C. and 50 mL of water was added thereto. Thereafter, extraction was performed with Vertrel XF, and the organic layer was washed with water and dehydration was performed with anhydrous sodium sulfate. The desiccant was filtered off. Thereafter, the filtrate was concentrated. The residue was purified by silica gel column chromatography to obtain 3.85 g of Compound (I).

$^1$H-NMR measurement of the obtained Compound (I) was conducted, and a structure was identified from the following results.

Compound (I); $^1$H-NMR (CD$_3$COCD$_3$)

δ [ppm] 0.90 to 1.20 (3H), 1.60 to 2.00 (2H), 3.55 to 4.20 (20H)

Example 7

3.55 g of Compound (J) was obtained by way of a compound represented by Formula (20) as an intermediate, by performing the same operation as in Example 6 except that 6.44 g of a compound represented by Formula (12), which was an intermediate synthesized in Example 3, was used instead of the compound represented by Formula (8).

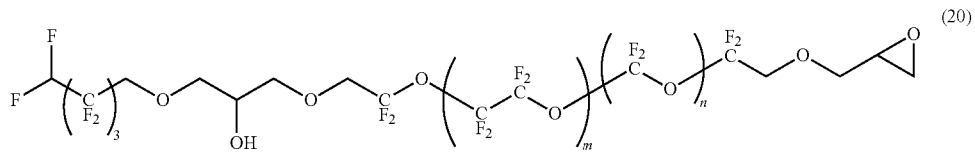

(In Formula (20), m indicating an average polymerization degree is 4.5 and n indicating an average polymerization degree is 4.5.)

$^1$H-NMR measurement of the obtained Compound (J) was conducted, and a structure was identified from the following results.

Compound (J); $^1$H-NMR (CD$_3$COCD$_3$);

δ [ppm] 1.60 to 2.00 (2H), 3.55 to 4.20 (20H) 6.10 (1H)

Example 6

5.51 g of the compound represented by Formula (8), which was the intermediate synthesized in Example 1, 50 mL of t-butanol, and 0.76 g of epibromohydrin were charged into a 200-mL eggplant flask under a nitrogen gas atmosphere, and stirred to be homogeneous. 0.168 g of potassium tert-butoxide was added to the homogeneous solution, and stirred at 70° C. for 6 hours to be reacted. The obtained reaction product was cooled to 25° C. and 50 mL of water was added thereto. Extraction was performed with Vertrel XF, and the organic layer was washed with water. This was dehydrated with anhydrous sodium sulfate. The desiccant was filtered off Thereafter, the filtrate was concentrated. The residue was purified by silica gel column chromatography to obtain 5.00 g of a compound represented by Formula (19) as an intermediate.

Example 8

5.00 g of the compound represented by Formula (19), which was the intermediate synthesized in Example 6, 28 mL of t-butanol, and 4.00 g of 2,2,3,3-tetrafluorobutane-1,4-diol were charged into a 100-mL eggplant flask under a

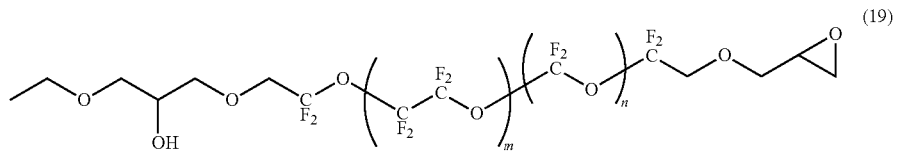

(In Formula (19), m indicating an average polymerization degree is 4.5 and n indicating an average polymerization degree is 4.5.)

nitrogen gas atmosphere, and stirred to be homogeneous. 0.168 g of potassium tert-butoxide was added to the homogeneous solution, and stirred at 70° C. for 6 hours to be reacted. The obtained reaction product was cooled to 25° C. and neutralized with 0.1 mol/L hydrochloric acid. Thereafter, extraction was performed with Vertrel XF, and the organic layer was washed with water and dehydration was performed with anhydrous sodium sulfate. The desiccant was filtered off. Thereafter, the filtrate was concentrated. The residue was purified by silica gel column chromatography to obtain 2.90 g of Compound (K).

$^1$H-NMR measurement of the obtained Compound (K) was conducted, and a structure was identified from the following results.

Compound (K); $^1$H-NMR (CD$_3$COCD$_3$);
δ [ppm] 0.90 to 1.20 (3H), 3.55 to 4.20 (20H)

Example 9

3.31 g of Compound (L) was obtained by performing the same operation as in Example 8, except that 5.78 g of a compound represented by Formula (20), which was an intermediate synthesized in Example 7, was used instead of the compound represented by Formula (19).

$^1$H-NMR measurement of the obtained Compound (L) was conducted, and a structure was identified from the following results.

Compound (L); $^1$H-NMR (CD$_3$COCD$_3$);
δ [ppm] 3.55 to 4.20 (20H), 6.10 (1H)

Example 10

3-Butenyl acetate (12.0 g) and 100 mL of dichloromethane were charged into a 500 mL eggplant flask, and stirred at room temperature to obtain a homogeneous solution. 31.0 g of m-chloroperbenzoic acid was added to the homogeneous solution under ice cooling, stirred at the same temperature for 1 hour, and further stirred at room temperature for 10 hours. Thereafter, 20 mL of a saturated aqueous sodium bicarbonate solution and 20 mL of a saturated aqueous sodium sulfite solution were added thereto under ice cooling, and stirred at the same temperature for 30 minutes. The aqueous layer was separated from the reaction solution. The organic layer was washed with water and dehydration was performed with anhydrous sodium sulfate. The desiccant was filtered off. Thereafter, the filtrate was concentrated. The residue was purified by silica gel column chromatography to obtain 6.40 g of a compound represented by Formula (21).

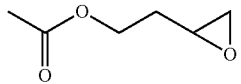

(21)

$^1$H-NMR measurement of the obtained Compound (21) was conducted, and a structure was identified from the following results.

Compound (21) $^1$H-NMR (CD$_3$COCD$_3$);
δ [ppm] 1.73 (1H), 1.88 (1H), 2.01 (3H), 2.41 (1H), 2.67 (1H), 2.88 (1H), 4.12 (2H)

5.51 g of the compound represented by Formula (8), which is the intermediate synthesized in Example 1, 0.781 g of the compound represented by Formula (21), and 50 mL of t-butanol were charged into a 200-mL eggplant flask under a nitrogen gas atmosphere, and stirred at room temperature to be homogeneous. 0.168 g of potassium tert-butoxide was added to the homogeneous solution, and stirred at 70° C. for 48 hours to be reacted. The obtained reaction product was cooled to 25° C., neutralized with 0.1 mol/L hydrochloric acid, and then extracted with Vertrel XF. The organic layer was washed with water and dehydrated with anhydrous sodium sulfate. The desiccant was filtered off. Thereafter, the filtrate was concentrated.

30 mL of methanol and 30 mL of 1 mol/L sodium hydroxide aqueous solution were added to the obtained residue at room temperature and stirred at room temperature for 1 hour. The methanol was distilled off, extraction was performed with Vertrel XF. The organic layer was washed with water and dehydration was performed with anhydrous sodium sulfate. The desiccant was filtered off Thereafter, the filtrate was concentrated. The residue was purified by silica gel column chromatography to obtain 3.21 g of Compound (M).

$^1$H-NMR measurement of the obtained Compound (M) was conducted, and a structure was identified from the following results.

Compound (M); $^1$H-NMR (CD$_3$COCD$_3$);
δ [ppm] 0.90 to 1.20 (3H), 1.60 to 2.00 (2H), 3.60 to 4.15 (16H)

Example 11

3.72 g of Compound (N) was obtained by performing the same operation as in Example 10, except that 6.44 g of a compound represented by Formula (12), which was an intermediate synthesized in Example 3, was used instead of the compound represented by Formula (8).

$^1$H-NMR measurement of the obtained Compound (N) was conducted, and a structure was identified from the following results.

Compound (N); $^1$H-NMR (CD$_3$COCD$_3$);
δ [ppm] 1.60 to 2.00 (2H), 3.60 to 4.15 (16H), 6.10 (1H)

Example 12

4.41 g of Compound (O) was obtained by performing the same operation as in Example 4, except that 20 g of a compound represented by HOCH$_2$CF$_2$CF$_2$O(CF$_2$CF$_2$CF$_2$O)$_{v1}$CF$_2$CF$_2$CH$_2$OH (in the formula, v1 indicating an average polymerization degree represents 4.5) was used instead of the compound represented by HOCH$_2$CF$_2$O(CF$_2$CF$_2$O)$_{m1}$(CF$_2$O)$_{n1}$CF$_2$CH$_2$OH (in the formula, m1 indicating an average polymerization degree represents 4.5 and n1 indicating an average polymerization degree represents 4.5).

$^1$H-NMR measurement of the obtained Compound (O) was conducted, and a structure was identified from the following results.

Compound (O); $^1$H-NMR (CD$_3$COCD$_3$):
δ [ppm]=2.40 (2H), 3.60 to 3.15 (20H)

Example 13

3.84 g of Compound (P) was obtained by performing the same operation as in Example 1, except that 2.02 g of a compound represented by Formula (22) was used instead of the compound represented by Formula (7).

The compound represented by Formula (22) was obtained by a reaction between 2-methoxyethoxymethyl chloride and glycidol in the presence of a base.

$^1$H-NMR measurement of the obtained Compound (P) was conducted, and a structure was identified from the following results.

Compound (P); $^1$H-NMR (CD$_3$COCD$_3$);
δ [ppm] 3.40 (3H), 3.55 to 4.20 (22H), 4.70 (2H)

Example 14

4.79 g of Compound (R) was obtained by performing the same operation as in Example 1, except that 5.76 g of a compound represented by Formula (23) was used instead of the compound represented by Formula (7).

The compound represented by Formula (23) was obtained by methylating one hydroxyl group of 1H, 1H, 11H, 11H-dodecafluoro-3,6,9-trioxaundecane-1,11-diol and reacting the other hydroxyl group with epibromohydrin.

$^1$H-NMR measurement of the obtained Compound (R) was conducted, and a structure was identified from the following results.

Compound (R); $^1$H-NMR (CD$_3$COCD$_3$);

δ [ppm] 3.40 (3H), 3.55 to 4.20 (22H)

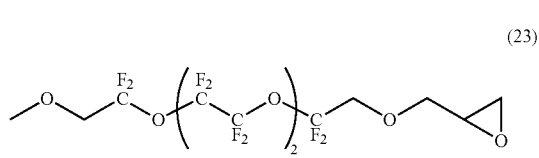

(23)

Example 15

4.44 g of Compound (T) was obtained by performing the same operation as in Example 1, except that the compound represented by Formula (23) was used instead of the compound represented by Formula (7), the compound represented by Formula (18) was used instead of the compound represented by Formula (9), and 10 mL of trifluoroacetic acid was used instead of the 20 g of 10% hydrogen chloride-methanol solution.

$^1$H-NMR measurement of the obtained Compound (T) was conducted, and a structure was identified from the following results.

Compound (T); $^1$H-NMR (CD$_3$COCD$_3$);

δ [ppm] 3.40 (3H), 3.55 to 4.20 (27H)

Example 16

4.51 g of Compound (U) was obtained by performing the same operation as in Example 15, except that a compound represented by Formula (24) was used instead of the compound represented by Formula (23).

$^1$H-NMR measurement of the obtained Compound (U) was conducted, and a structure was identified from the following results.

Compound (U); $^1$H-NMR (CD$_3$COCD$_3$);

δ [ppm] 3.40 (3H), 3.55 to 4.20 (32H)

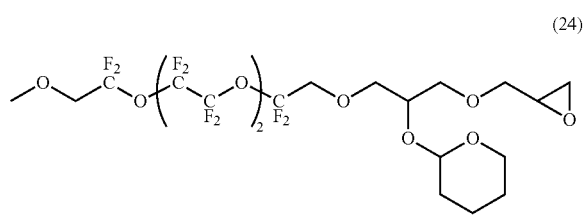

(24)

The compound represented by Formula (24) was obtained from epibromohydrin and a compound in which, after protecting the primary hydroxyl group of a compound obtained by hydrolyzing the epoxy group of the compound represented by Formula (23) with a tert-butyldimethylsilyl (TBS) group, and subsequently protecting the secondary hydroxyl group with a tetrahydropyranyl (THP) group, the TBS group was deprotected.

Comparative Example 1

Fomblin Z-tetraol (molecular weight about 2000) (manufactured by Solvey Solexis corporation) represented by Formula (X) was used.

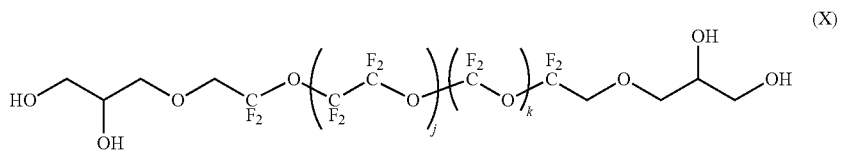

(X)

(In Formula (X), j represents 10 and k represents 10.)

Comparative Example 2

A compound represented by Formula (Y) was synthesized by the method described in Patent Document 1.

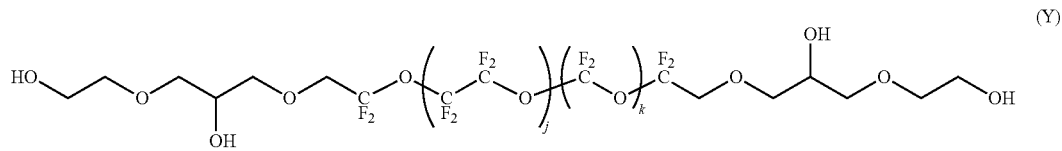

(Y)

(In Formula (Y), j represents 4.5 and k represents 4.5.)

Comparative Example 3

A compound represented by Formula (Z) was synthesized by the method described in Patent Document 2.

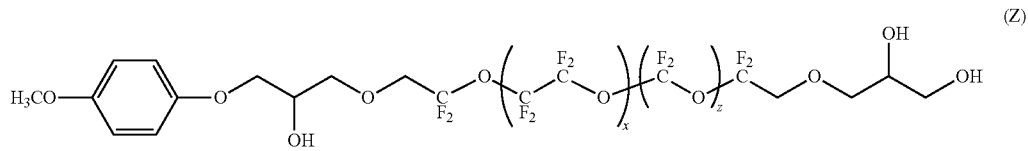

(In Formula (Z), x represents 4.5 and z represents 4.5.)

Comparative Example 4

A compound represented by Formula (W) was synthesized by the method described in Patent Document 4.

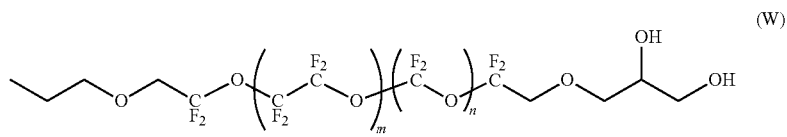

(In Formula (W), m represents 4.5 and n represents 4.5.)

Tables 1 and 2 show the structures of $R^1$ to $R^4$ when the compounds of Examples 1 to 16 obtained as above were applied to Formula (1). The number-average molecular weights (Mn) of the compounds of Examples 1 to 16 were determined by the $^1$H-NMR and $^{19}$F-NMR measurements described above. Results thereof are shown in Tables 1 and 2.

TABLE 1

| Example | $R^1$ | $R^2$ | $R^3$ | $R^4$ | Mn |
|---|---|---|---|---|---|
| 1 | (propyl) | Formula (6) w = 1 | Formula (3) m = 4.5 n = 4.5 | Formula (2-1) p1 = 1 p2 = 1 | 1217 |
| 2 | (pentyl) | Formula (6) w = 1 | Formula (3) m = 4.5 n = 4.5 | Formula (2-1) p1 = 1 p2 = 1 | 1245 |
| 3 | F$_2$CF–(CF$_2$)$_3$– | Formula (6) w = 1 | Formula (3) m = 4.5 n = 4.5 | Formula (2-1) p1 = 1 p2 = 1 | 1403 |
| 4 | F$_3$C–(CF$_2$)$_5$– | Formula (6) w = 1 | Formula (3) m = 4.5 n = 4.5 | Formula (2-1) p1 = 1 p2 = 1 | 1535 |
| 5 | F$_3$C–CF$_2$–CF$_2$– | O | Formula (3) m = 4.5 n = 4.5 | Formula (2-1) p1 = 2 p2 = 1 | 1435 |
| 6 | (propyl) | Formula (6) w = 1 | Formula (3) m = 4.5 n = 4.5 | Formula (2-4) q = 2 | 1231 |
| 7 | F$_2$CF–(CF$_2$)$_3$– | Formula (6) w = 1 | Formula (3) m = 4.5 n = 4.5 | Formula (2-4) q = 2 | 1417 |

TABLE 2

| Example | R$^1$ | R$^2$ | R$^3$ | R$^4$ | Mn |
|---|---|---|---|---|---|
| 8 | (branched alkyl) | Formula (6) w = 1 | Formula (3) m = 4.5 n = 4.5 | Formula (2-2) s = 2 | 1317 |
| 9 | CF$_3$-CF$_2$-(CF$_2$)$_3$- (fluorinated alkyl) | Formula (6) w = 1 | Formula (3) m = 4.5 n = 4.5 | Formula (2-2) s = 2 | 1503 |
| 10 | (branched alkyl) | Formula (6) w = 1 | Formula (3) m = 4.5 n = 4.5 | Formula (2-3) t = 1 | 1187 |
| 11 | CF$_3$-CF$_2$-(CF$_2$)$_3$- (fluorinated alkyl) | Formula (6) w = 1 | Formula (3) m = 4.5 n = 4.5 | Formula (2-3) t = 1 | 1373 |
| 12 | F$_3$C-(CF$_2$)$_5$-CH$_2$- | Formula (6) w = 1 | Formula (5) v = 4.5 | Formula (2-1) p1 = 1 p2 = 1 | 1563 |
| 13 | CH$_3$-O-CH$_2$CH$_2$-O-CH$_2$- | Formula (6) w = 1 | Formula (3) m = 4.5 n = 4.5 | Formula (2-1) p1 = 1 p2 = 1 | 1277 |
| 14 | CH$_3$-O-CF$_2$-O-(CF$_2$CF$_2$-O)$_2$-CF$_2$- | Formula (6) w = 1 | Formula (3) m = 4.5 n = 4.5 | Formula (2-1) p1 = 1 p2 = 1 | 1595 |
| 15 | CH$_3$-O-CF$_2$-O-(CF$_2$CF$_2$-O)$_2$-CF$_2$- | Formula (6) w = 1 | Formula (3) m = 4.5 n = 4.5 | Formula (2-1) p1 = 2 p2 = 1 | 1669 |
| 16 | CH$_3$-O-CF$_2$-O-(CF$_2$CF$_2$-O)$_2$-CF$_2$- | Formula (6) w = 2 | Formula (3) m = 4.5 n = 4.5 | Formula (2-1) p1 = 2 p2 = 1 | 1743 |

Next, a lubricating layer-forming solution was prepared using the compounds obtained in Examples 1 to 16 and Comparative Examples 1 to 4 by the method shown below. Then, according to the method shown below, the lubricating layer of the magnetic recording medium was formed using the obtained lubricating layer-forming solution, and the magnetic recording media of Examples 1 to 16 and Comparative Examples 1 to 4 were obtained.

"Lubricating Layer-forming Solution"

Each of the compounds obtained in Examples 1 to 16 and Comparative Examples 1 to 4 was dissolved in Vertrel (registered trademark) XF (trade name, manufactured by Du Pont-Mitsui Fluorochemicals Co., Ltd.) as a fluorinated solvent, was diluted with the Vertrel, such that the film thickness when applied to the protective layer was 9 Å to 11 Å, to obtain a lubricating layer-forming solution.

"Magnetic Recording Medium"

A magnetic recording medium, in which an adhesion layer, a soft magnetic layer, a first base layer, a second base layer, a magnetic layer, and a protective layer were provided in this order on a substrate having a diameter of 65 mm, was prepared. The protective layer was formed to include carbon.

The lubricating layer-forming solutions of Examples 1 to 16 and Comparative Examples 1 to 4 were respectively applied by a dip method onto the protective layer of the magnetic recording medium in which each layer up to the protective layer was formed. The dip method was performed under conditions of an immersion speed of 10 mm/sec, an immersion time of 30 sec, and a pulling speed of 1.2 mm/sec.

Thereafter, the magnetic recording medium to which the lubricating layer-forming solution was applied was placed in a thermostatic chamber at 120° C. and heated for 10 minutes to remove the solvent in the lubricating layer-forming solution. Accordingly, the lubricating layer was formed on the protective layer to form a magnetic recording medium.

The film thickness of a lubricating layer of each of the magnetic recording media obtained in this manner in Examples 1 to 16 and Comparative Examples 1 to 4 was measured using FT-IR (trade name: Nicolet iS50, manufactured by Thermo Fisher Scientific). The results thereof are shown in Table 3.

Next, a chemical resistance test to be shown below was conducted on the magnetic recording media of Examples 1 to 16 and Comparative Examples 1 to 4.

(Chemical Resistance Test)

For the evaluation method, an evaluation method in which contamination of the magnetic recording medium is investigated by using an environmental substance that produces contaminant in a high-temperature environment is used. In the evaluation method shown below, Si ions were used as the environmental substance, and an Si adsorption amount was measured as the amount of the contaminant which was formed by the environmental substance and contaminated the magnetic recording medium.

Specifically, the magnetic recording medium to be evaluated was kept for 240 hours in the presence of siloxane Si rubber under a high-temperature environment of a temperature of 85° C. and a humidity of 0%. Next, the Si adsorption amount on the surface of the magnetic recording medium was analyzed and measured using secondary ion mass spectrometry (SIMS), and the degree of contamination due to the Si ions was evaluated as the Si adsorption amount. In the evaluation of the Si adsorption amount, evaluation was performed by using the numerical value when the result of Comparative Example 2 is 1.00. The results thereof are shown in Table 3.

TABLE 3

|  | Compound | Film Thickness (Å) | Chemical resistance | Time until coefficient of friction increases (sec) |
| --- | --- | --- | --- | --- |
| Example 1 | A | 9.5 | 0.71 | B |
| Example 2 | C | 9.5 | 0.71 | B |
| Example 3 | F | 9.5 | 0.66 | A |
| Example 4 | G | 9.0 | 0.64 | A |
| Example 5 | H | 9.0 | 0.66 | B |
| Example 6 | I | 9.0 | 0.69 | B |
| Example 7 | J | 9.5 | 0.63 | A |
| Example 8 | K | 9.0 | 0.70 | A |
| Example 9 | L | 9.5 | 0.61 | A |
| Example 10 | M | 9.5 | 0.68 | B |
| Example 11 | N | 9.0 | 0.62 | A |
| Example 12 | O | 9.5 | 0.70 | B |
| Example 13 | P | 9.0 | 0.68 | B |
| Example 14 | R | 9.5 | 0.68 | A |
| Example 15 | T | 9.0 | 0.64 | A |
| Example 16 | U | 9.0 | 0.59 | A |
| Comparative Example 1 | X | 10.5 | 0.80 | D |
| Comparative Example 2 | Y | 10.0 | 1.00 | C |
| Comparative Example 3 | Z | 10.0 | 1.02 | C |
| Comparative Example 4 | W | 10.0 | 0.99 | C |

As shown in Table 3, it became clear that the magnetic recording media of Examples 1 to 16 have a small Si adsorption amount and are less likely to be contaminated by the environmental substance under high-temperature environment, even when a film thickness of the lubricating layer is reduced, as compared to the magnetic recording media of Comparative Examples 1 to 4.

Further, in Comparative Example 2, in Compound (Y) forming the lubricating layer, when applied to Formula (1), the carbon atoms bonded to the hydroxyl groups in $R^4$ are bonded to each other via a linking group containing a carbon atom not bonded to a hydroxyl group. Therefore, from the results of Examples 1 to 16 and Comparative Example 2 shown in Table 3, it was found that in the compound forming the lubricating layer, in a case where $R^1$ when applied to Formula (1) is an alkyl group that may have a substituent, chemical resistance is improved.

In addition, a wear resistance test to be shown below was conducted on the magnetic recording media of Examples 1 to 16 and Comparative Examples 1 to 4.

(Wear Resistance Test)

Using a pin-on-disk type friction and wear tester, an alumina ball having a diameter of 2 mm as a contact was slid on the lubricating layer of the magnetic recording medium, with a load of 40 gf at a sliding speed of 0.25 m/sec, to measure a coefficient of friction of a surface of the lubricating layer. Then, sliding time until the coefficient of friction of the surface of the lubricating layer sharply increases was measured. The sliding time until the coefficient of friction sharply increases was measured four times for each lubricating layer of the magnetic recording medium, and an average value (time) thereof was used as an indicator of the wear resistance of the lubricant coating film. Table 3 shows the results of the magnetic recording media using the compounds of Examples 1 to 16 and the compounds of Comparative Examples 1 to 4. The evaluation of time until the coefficient of friction increases was as follows.

A (Excellent): 650 sec or more
B (Favorable): 550 sec or more and less than 650 sec
C (Allowable): 450 sec or more and less than 550 sec
D (Unallowable): Less than 450 sec The time until the coefficient of friction sharply increases can be used as an indicator of the wear resistance of the lubricating layer for the following reason. In the lubricating layer of the magnetic recording medium, wear progresses according to use of the magnetic recording medium. When the lubricating layer disappears due to the wear, the contact and the protective layer are in direct contact with each other to cause the coefficient of friction to sharply increase. The time until the coefficient of friction sharply increases is considered to have a correlation with the friction test.

As shown in Table 3, the magnetic recording media of Examples 1 to 16 have a longer sliding time until the coefficient of friction sharply increases, and were more favorable in wear resistance, even when a film thickness of the lubricating layer is reduced, as compared to the magnetic recording medium of Comparative Examples 1 to 4.

It is presumed that this is because, in the magnetic recording medium of Examples 1 to 16, in the compound represented by Formula (1) forming the lubricating layer, $R^1$ is an alkyl group that may have a substituent, $R^4$ is an end group which is different from $R^1$-$R^2$ and includes two or three hydroxyl groups, in which each of the hydroxyl groups is bonded to a different carbon atom, and the carbon atoms bonded to the hydroxyl groups are bonded to each other via a linking group containing a carbon atom not bonded to the hydroxyl group.

INDUSTRIAL APPLICABILITY

When using the lubricant for a magnetic recording medium including the fluorine-containing ether compound of the present invention, it is possible to form a lubricating layer in which excellent chemical resistance and wear resistance can be realized even when a thickness thereof is reduced.

That is, according to the present invention, it is possible to provide a fluorine-containing ether compound which can form a lubricating layer having excellent chemical resistance and wear resistance, even when the thickness is reduced, and can be suitably used as a material of a lubricant for a magnetic recording medium.

REFERENCE SIGNS LIST

10 . . . Magnetic recording medium
11 . . . Substrate

12 ... Adhesion layer
13 ... Soft magnetic layer
14 ... First base layer
15 ... Second base layer
16 ... Magnetic layer
17 ... Protective layer
18 ... Lubricating layer

The invention claimed is:

1. A fluorine-containing ether compound represented by Formula (1)

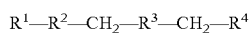  (1)

(in Formula (1), $R^1$ is an alkyl group that may have a substituent, $R^2$ is represented by —O— or Formula (6)

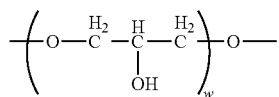  (6)

(in Formula (6), w represents 1 to 4), $R^3$ is a perfluoropolyether chain, and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups).

2. The fluorine-containing ether compound according to claim 1,
wherein the polar groups of $R^4$ in Formula (1) are hydroxyl groups.

3. A fluorine-containing ether compound represented by Formula (1),

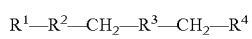  (1)

(in Formula (1), $R^1$ is an alkyl group that may have a substituent, $R^2$ is a divalent linking group bonded to $R^1$ via an ethereal oxygen, $R^3$ is a perfluoropolyether chain, and
$R^4$ is an end group represented by any one of Formulas (2-1) to (2-4)

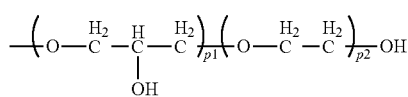  (2-1)

(in Formula (2-1), p1 represents 1 to 2 and p2 represents 1 to 5),

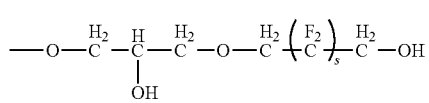  (2-2)

(in Formula (2-2), s represents 2 to 5),

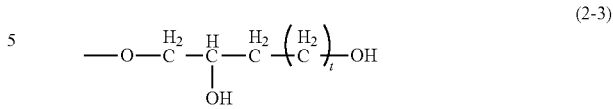  (2-3)

(in Formula (2-3), t represents 1 to 5),

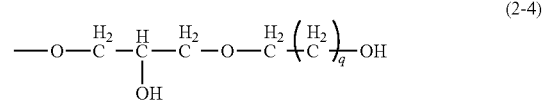  (2-4)

(in Formula (2-4), q represents 2 to 5).

4. A fluorine-containing ether compound represented by Formula (1),

  (1)

in Formula (1), $R^1$ is an alkyl group that may have a substituent, $R^2$ is a divalent linking group bonded to $R^1$ via an ethereal oxygen, $R^3$ is represented by Formula (3), (4) or (5),

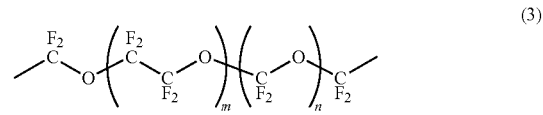  (3)

(in Formula (3), m and n represent average polymerization degrees, m represents 1 to 30, and n represents 0 to 30),

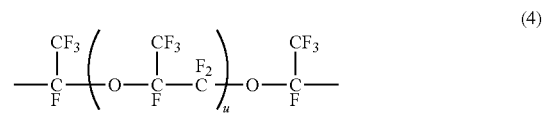  (4)

in Formula (4), u represents an average polymerization degree and represents 1 to 30),

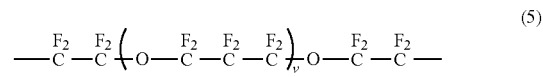  (5)

in Formula (5), v represents an average polymerization degree and represents 1 to 30), and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups).

5. A fluorine-containing ether compound represented by Formula (1),

  (1)

in Formula (1) $R^1$ is an alkyl group in which a part or all of hydrogen atoms are substituted with halogen and an alkoxy group or with either halogen or an alkoxy group, $R^2$ is a divalent linking group bonded to $R^1$ via an ethereal oxygen, $R^3$ is a perfluoropolyether chain, and $R^4$ is an end group which is different from $R^1$-$R^2$ and includes two or three polar groups, in which each of the polar groups is bonded to a different carbon atom, and the carbon atoms bonded to the polar groups are bonded to each other via a linking group containing a carbon atom not bonded to the polar groups).

6. The fluorine-containing ether compound according to claim 1, wherein $R^4$ in Formula (1) includes three polar groups.

7. The fluorine-containing ether compound according to claim 1, wherein a number-average molecular weight thereof is in a range of 500 to 10000.

8. A lubricant for a magnetic recording medium, comprising:
the fluorine-containing ether compound according to claim 1.

9. A magnetic recording medium, comprising:
a substrate; and
at least a magnetic layer, a protective layer, and a lubricating layer in this order on the substrate,
wherein the lubricating layer includes the fluorine-containing ether compound according to claim 1.

10. The magnetic recording medium according to claim 9, wherein an average film thickness of the lubricating layer is 0.5 nm to 3 nm.

11. A lubricant for a magnetic recording medium, comprising:
the fluorine-containing ether compound according to claim 3.

12. A magnetic recording medium, comprising:
a substrate; and
at least a magnetic layer, a protective layer, and a lubricating layer in this order on the substrate,
wherein the lubricating layer includes the fluorine-containing ether compound according to claim 3.

13. A lubricant for a magnetic recording medium, comprising:
the fluorine-containing ether compound according to claim 4.

14. A magnetic recording medium, comprising:
a substrate; and
at least a magnetic layer, a protective layer, and a lubricating layer in this order on the substrate,
wherein the lubricating layer includes the fluorine-containing ether compound according to claim 4.

15. A lubricant for a magnetic recording medium, comprising:
the fluorine-containing ether compound according to claim 5.

16. A magnetic recording medium, comprising:
a substrate; and
at least a magnetic layer, a protective layer, and a lubricating layer in this order on the substrate,
wherein the lubricating layer includes the fluorine-containing ether compound according to claim 5.

* * * * *